(12) United States Patent
Bhat et al.

(10) Patent No.: US 10,035,761 B2
(45) Date of Patent: *Jul. 31, 2018

(54) COMPOSITIONS, SYNTHESIS, AND METHODS OF USING PHENYLCYCLOALKYLMETHYLAMINE DERIVATIVES

(71) Applicant: Reviva Pharmaceuticals, Inc., Santa Clara, CA (US)

(72) Inventors: Laxminarayan Bhat, Cupertino, CA (US); Kouacou Adiey, San Jose, CA (US); Seema Rani Bhat, Cupertino, CA (US)

(73) Assignee: Revivia Pharmaceuticals, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/639,135

(22) Filed: Jun. 30, 2017

(65) Prior Publication Data
US 2018/0127362 A1    May 10, 2018

Related U.S. Application Data

(63) Continuation of application No. 14/986,267, filed on Dec. 31, 2015, now Pat. No. 9,695,116, which is a continuation of application No. 13/731,670, filed on Dec. 31, 2012, now Pat. No. 9,238,625.

(60) Provisional application No. 61/582,201, filed on Dec. 30, 2011.

(51) Int. Cl.
| | |
|---|---|
| C07C 211/27 | (2006.01) |
| C07C 217/08 | (2006.01) |
| C07C 217/74 | (2006.01) |
| C07C 323/25 | (2006.01) |
| C07C 323/32 | (2006.01) |
| C07C 317/28 | (2006.01) |
| C07C 211/29 | (2006.01) |
| C07C 317/18 | (2006.01) |

(52) U.S. Cl.
CPC .......... *C07C 317/28* (2013.01); *C07C 211/27* (2013.01); *C07C 211/29* (2013.01); *C07C 217/08* (2013.01); *C07C 217/74* (2013.01); *C07C 317/18* (2013.01); *C07C 323/25* (2013.01); *C07C 323/32* (2013.01); *C07C 2601/02* (2017.05); *C07C 2601/04* (2017.05); *C07C 2601/08* (2017.05); *C07C 2601/14* (2017.05)

(58) Field of Classification Search
CPC ... C07C 211/27; C07C 217/08; C07C 217/74; C07C 323/25; C07C 323/32
See application file for complete search history.

(56) References Cited

U.S. PATENT DOCUMENTS

| | | |
|---|---|---|
| 4,629,727 A | 12/1986 | Kozlik et al. |
| 5,015,664 A | 5/1991 | Green |
| 7,989,500 B2 | 8/2011 | Bhat et al. |
| 8,227,476 B2 | 7/2012 | Ceci et al. |
| 8,445,714 B2 | 5/2013 | Bhat et al. |
| 9,238,625 B2 | 1/2016 | Bhat et al. |
| 9,695,116 B2 | 7/2017 | Bhat et al. |
| 2002/0183554 A1 | 12/2002 | Senanayake |
| 2010/0267945 A1 | 10/2010 | Okuno et al. |
| 2010/0273841 A1 | 10/2010 | Okuno et al. |
| 2010/0273842 A1 | 10/2010 | Okuno et al. |
| 2011/0263888 A1 | 10/2011 | Bhat et al. |
| 2012/0172426 A1 | 7/2012 | Bhat et al. |

FOREIGN PATENT DOCUMENTS

| | | |
|---|---|---|
| EP | 0111994 A1 | 6/1984 |
| EP | 0191542 A1 | 8/1986 |
| EP | 1595873 A1 | 11/2005 |
| GB | 2127819 A | 4/1984 |
| JP | 2007-254409 A | 10/2007 |
| WO | 2002068420 A1 | 9/2002 |
| WO | 2004058237 A1 | 7/2004 |
| WO | 2005037214 A3 | 4/2005 |
| WO | 2007081857 A2 | 7/2007 |
| WO | 2008-034142 A2 | 3/2008 |
| WO | 2009057079 A2 | 5/2009 |
| WO | 2010-122968 A1 | 10/2010 |
| WO | 2012003501 A2 | 1/2012 |

OTHER PUBLICATIONS

International Search Report and Written Opinion of PCT Application No. PCT/US2012/072283 dated May 15, 2013.

*Primary Examiner* — Sahar Javanmard
(74) *Attorney, Agent, or Firm* — Perkins Coie LLP; Viola T. Kung

(57) ABSTRACT

The present invention provides novel phenylcycloalkylmethylamine derivatives, and methods of preparing phenylcycloalkylmethylamine derivatives. The present invention also provides methods of using phenylcycloalkylmethylamine derivatives and compositions of phenylcycloalkylmethylamine derivatives. The pharmaceutical compositions of the compounds of the present invention can be used for treating and/or preventing obesity and obesity related co-morbid indications and depression and depression related co-morbid indications.

13 Claims, No Drawings

COMPOSITIONS, SYNTHESIS, AND METHODS OF USING PHENYLCYCLOALKYLMETHYLAMINE DERIVATIVES

This application is a continuation of U.S. patent application Ser. No. 14/986,267, filed Dec. 31, 2015; which is a continuation of U.S. patent application Ser. No. 13/731,670, filed Dec. 31, 2012, now U.S. Pat. No. 9,238,625; which claims priority to U.S. Provisional Application No. 61/582,201, filed Dec. 30, 2011; the contents of the above identified applications are incorporated herein by reference in their entirety.

TECHNICAL FIELD

The present invention relates to phenylcycloalkylmethylamine derivatives, synthesis of phenylcycloalkylmethylamine derivatives and methods of using phenylcycloalkylmethylamine derivatives for the pharmacological treatment of obesity, depression and obesity related co-morbid indications.

BACKGROUND

Obesity is a chronic disease that affects millions of people across the world especially in the developed countries. It is defined by excess body fat and is generally measured by calculating a person's BMI (body mass index). If a person's BMI is 30 or above, he or she considered to be obese. Obesity can cause a number of health problems either directly or indirectly, such as, for example, type 2 diabetes, coronary heart disease, high blood triglycerides, high blood pressure and stroke. Obesity also raises risk of certain types of cancer. Obese men are more likely than normal-weight peers to die from cancer of the colon, rectum, and prostate. Obese women are more likely than non-obese women to die from cancer of the gallbladder, breast, uterus, cervix and ovaries. Death from some cancers may be more likely because obesity makes the cancers harder to detect in the early stages (for example, the initial small lump of breast cancer may not be felt in an obese woman). Recent studies show obesity increases the risk of Alzheimer's-type dementia. Other disease and health problems linked to obesity include: gallbladder disease, gallstones, osteoarthritis, gout or joint pain, sleep apnea, psychological and social problems.

Obesity is caused by multiple factors, the primary factor being genetics which is the one factor relating to obesity over which individuals have no control. Other important factors involved in obesity are: the mechanisms of fat storage; the balance between energy intake and energy expenditure; an individual's life style: eating habits and exercise; and psychological, cultural and socioeconomic influences. Despite the seeming inexorable progression of this disease, there have been limited advances in the pharmacotherapy of this condition. Drugs to treat obesity can be divided into three groups: those that reduce food intake or appetite suppressants; those that alter metabolism or block the absorption of fat; and those that increase thermogenesis. Currently, there are only two drugs approved by the FDA for the long-term treatment of obesity and they are fat absorption blocker orlistat (XENICAL®) and the appetite suppressant sibutramine (MERIDIA®). The only thermogenic drug combination that has been tested is ephedrine and caffeine, but this treatment has not been approved by regulatory agencies.

The fat absorption blocker, orlistat works in the gastrointestinal tract by blocking an enzyme that is needed to digest fat. Instead of being absorbed from the intestine, up to one-third of the fat that a person consumes is excreted in the stool. In addition, orlistat blocks the absorption of needed fat-soluble vitamins A, D, E, and K, as well as beta-carotene. This is one of the major limitations of this drug for the long term use in the treatment of obesity. Most commonly reported other side effects of orlistat are bloating, diarrhea and oily stools.

In the appetite suppressant category, a few noradrenergic and serotonergic drugs belong to a family of 2-arylethylamines are currently available in the market for the treatment of obesity. The noradrenergic agents such as phenylpropanolamine, (ACUTRIM®, DEXATRIM®), diethylpropion (TENUATE®), and phentermine (FASTIN®, IONAMIN®) are approved for the short-term treatment of obesity. Whereas, noradrenergic and serotonergic agent sibutramine (MERIDIA®) is the only drug currently approved for the long-term treatment of obesity in the appetite suppressant category. Sibutramine has cyclobutanemethylamine backbone and it is this backbone mainly responsible for its unique pharmacological properties.

In the last 10 years, a number of reports have been published on the possible use of sibutramine, either alone or in combination with other therapeutic agents, for the treatment and/or prevention of a variety diseases and/or disorders in addition to obesity (see, Montana, J. G., WO 2004/058237; Lulla, A. et al., WO 2004/096202; Jerussi, T. P. et al., WO 02/060424; Senanayake, C. H. et al., WO 01/51453; Heal, D. J., WO 01/00205; Birch, A. M. et al., WO 01/00187; Mueller, P., WO 00/32178; Bailey, C., WO 98/11884; Kelly, P., WO 98/13034). For examples: treatment of nausea, emesis, and related conditions; cognitive dysfunctions; eating disorders; weight gain; irritable bowel syndrome; obsessive compulsive disorders; platelet adhesion; apnea, affective disorders such as attention deficit disorders, depression, and anxiety; male and female sexual function disorders; restless leg syndrome; osteoarthritis; substance abuse including nicotine and cocaine addiction; narcolepsy; pain such as neuropathic pain, diabetic neuropathy, and chronic pain; migraines; cerebral function disorders; chronic disorders such as premenstrual syndrome; and incontinence.

In general, sibutramine has a number of therapeutic benefits because of its unique pharmacological properties. However, sibutramine's therapeutic use for the treatment of obesity, and other diseases and disorders is currently not fully utilized because of certain limitations and adverse side effects associated with the drug. The major adverse events reported, in some cases life threatening, include increase in blood pressure and the side effects derived from the drug-drug interactions, for example, serotonin syndrome. The majority of these adverse events are, to some extent, metabolism-based. Sibutramine exerts its pharmacological actions predominantly via its secondary ($M_1$) and primary ($M_2$) amine metabolites. Sibutramine is metabolized in the liver principally by the cytochrome P450 (3A4) isozymes, to desmethyl metabolites, $M_1$ and $M_2$. These active metabolites are further metabolized by hydroxylation and conjugation to pharmacologically inactive metabolites, $M_5$ and $M_6$. The elimination half-lives of therapeutically active primary and secondary metabolites $M_1$ and $M_2$ are 14 and 16 hours, respectively. It is evident from a number literature reports that cytochrome P450 mediated metabolism and the long half lives of active metabolites ($M_1$ and $M_2$) are to a great extent responsible for adverse events such as increased blood pressure and other side effects derived from drug-drug interactions of sibutramine.

Therefore, there is a need and great demand for safer and effective next generation appetite suppressants for the treatment of obesity. An ideal drug in this class should have potent appetite suppressant activity, a proven effect on fat loss, be well tolerated during acute and chronic administration and have alleviated side effects when compared to sibutramine and phentermine.

SUMMARY OF THE INVENTION

The present invention is directed towards compositions of novel phenylcycloalkylmethylamine derivatives and the use of the compositions for the treatment of obesity, and related co-morbid conditions and depression and related co-morbid conditions. The present invention provides methods for synthesizing such phenylcycloalkylmethylamine derivatives. The present invention also provides methods for using phenylcycloalkylmethylamine derivatives and pharmaceutical composition of phenylcycloalkylmethylamine derivatives for treating or preventing obesity and co-morbid diseases and/or disorders and for treating or preventing depression and co-morbid diseases and/or disorders.

The compounds of the present disclosure are advantageous because of their favorable metabolic, pharmacokinetics and pharmacological profiles.

The present invention provides phenylcycloalkylmethylamine derivatives of structural Formula (I):

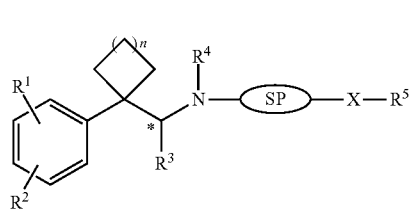

(I)

or isomer or pharmaceutically acceptable salt thereof, wherein:

n is 0, 1, 2, 3, 4, or 5;

SP is a spacer, wherein the spacer is $C_{1-6}$ alkylene, and wherein one or more of the carbons of the $C_{1-6}$ alkylene is optionally substituted with O, S, or $NR^6$, wherein $R^6$ is H or $C_{1-6}$ alkyl;

X is O, S, $NR^6$ or S(O)(O);

$R^1$, $R^2$, $R^3$, $R^4$, and $R^5$ are each independently hydrogen, $C_{1-6}$ alkyl, aryl, arylalkyl, cycloalkyl, cycloheteroalkyl, heteroaryl, heteroarylalkyl, acylalkyloxycarbonyl, acyloxyalkyloxycarbonyl, acylalkyloxycarbonylamino, acyloxyalkyloxycarbonylamino, $C_{1-6}$ alkoxy, alkoxycarbonyl, alkoxycarbonylalkoxy, alkoxycarbonylalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$, $R^2$, $R^3$, $R^4$, and $R^5$ is substituted with the isotopes $^2H$ (deuterium), $^3H$ (tritium), $^{13}C$, $^{15}N$, $^{17}O$, $^{18}O$, $^{18}F$, $^{31}P$, $^{32}P$, $^{35}S$, and $^{36}Cl$; and "*" denotes a carbon capable of being optically active.

The compounds of the present disclosure include (R)-isomers, (S)-isomers, and mixtures of (R)- and (S)-isomers.

DETAILED DESCRIPTION

This invention provides compounds, pharmaceutical compositions and methods for pharmacological treatment of obesity and related co-morbid diseases and/or disorders. This invention also provides methods for synthesis of novel appetite suppressants.

Definitions

The compounds of the invention may contain one or more chiral centers and/or double bonds and therefore, may exist as stereoisomers, such as double-bond isomers (i.e., geometric isomers), enantiomers or diastereoisomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass of conventionally found in nature. Examples of isotopes that may be incorporated into the compounds of the invention include, but are not limited to $^2H$, $^3H$, $^{13}C$, $^{15}N$, $^{18}O$, $^{17}O$, $^{31}P$, $^{32}P$, $^{35}S$, $^{18}F$ and $^{36}Cl$.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to methyl; ethyls such as ethanyl, ethenyl, ethynyl; propyls such as propan-1-yl, propan-2yl, cyclopropan-1-yl, prop-1-en-1-yl, prop-1-en-2-yl, prop-2-en-1-yl (allyl), cycloprop-1-en-1yl, cycloprop-2-en-1yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1, 3-dien-1-yl, buta-1, 3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc. The term "$C_{1-6}$ alkyl" encompasses $C_1$ alkyl, $C_2$ alkyl, $C_3$ alkyl, $C_4$ alkyl, $C_5$ alkyl, and $C_6$ alkyl.

The term "alkyl" specifically intended to include radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkany," "alkenyl," and "alkynyl," are used. Preferably, an alkyl group comprises from 1-20 carbon atoms, more preferably, from 1 to 10 carbon atoms.

The term "alkylene" refers to the removal of a hydrogen atom from "alkanyl."

"Alkanyl" refers to a saturated branched, straight-chain or cyclic alkyl radical derived by the removal of one hydrogen atom from a single carbon atom of a parent alkane. Typical alkanyl groups include but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methy-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien 1-yl, etc.

"Alkylene" refers to a divalent radical that is a branched or unbranched hydrocarbon fragment containing the specified number of carbon atoms, and having two points of attachment. Alkylenes are optionally substituted with one, two or three substituents. The term "$C_{1-6}$ alkylene" encompasses $C_1$ alkylene, $C_2$ alkylene, $C_3$ alkylene, $C_4$ alkylene, $C_5$ alkylene, $C_6$ alkylene, and any sub-range thereof. Examples of alkylenes include without limitation: methylene (—$CH_2$—, a $C_1$ alkylene), ethylene (—$CH_2CH_2$—, a $C_2$ alkylene), propylene (—$CH_2CH_2CH_2$—, a $C_3$ alkylene), and butylene (—$CH_2CH_2CH_2CH_2$—, a $C_4$ alkylene).

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn3-yl, but-3-yn-1-yl, etc.

"Acyl" refers to a radical —C(O)R, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to formyl, acetyl, cyclohexylcarbonyl, cyclohexylmethylcarbonyl, benzoyl, benzylcarbonyl.

"Acyloxyalkyloxycarbonyl" refers to a radical —C(O)OCR'R"OC(O)R'", where R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$OC(O)CH$_3$, —C(O)OCH$_2$OC(O)CH$_2$CH$_3$, —C(O)OCH(CH$_3$)OC(O)CH$_2$CH$_3$, —C(O)OCH(CH$_3$)OC(O)C$_6$H$_5$.

"Acylalkyloxycarbonyl" refers to a radical —C(O)OCR'R"C(O)R'", where R', R", and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$C(O)CH$_3$, —C(O)OCH$_2$C(O)CH$_2$CH$_3$, —C(O)OCH(CH$_3$)C(O)CH$_2$CH$_3$, —C(O)OCH(CH$_3$)C(O)C$_6$H$_5$.

"Acyloxyalkyloxycarbonylamino" refers to a radical —NRC(O)OCR'R"OC(O)R'", where R, R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$OC(O)CH$_3$, —NHC(O)OCH$_2$OC(O)CH$_2$CH$_3$, —NHC(O)OCH(CH$_3$)OC(O)CH$_2$CH$_3$, —NHC(O)OCH(CH$_3$)OC(O)C$_6$H$_5$.

"Acylalkyloxycarbonylamino" refers to a radical —NRC(O)OCR'R"C(O)R'", where R, R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$C(O)CH$_3$, —NHC(O)OCH$_2$C(O)CH$_2$CH$_3$, —NHC(O)OCH(CH$_3$)C(O)CH$_2$CH$_3$, —NHC(O)OCH(CH$_3$)C(O)C$_6$H$_5$.

"Alkylamino" means a radical —NHR where R represents an alkyl, or cycloalkyl group as defined herein that may be optionally substituted by one or more substituents as defined herein. Representative examples include, but are not limited to, methylamino, ethylamino, 1-methylethylamino, cyclohexylamino.

"Alkoxy" refers to a radical —OR where R represents an alkyl, or cycloalkyl group as defined herein that may be optionally substituted by one or more substituents as defined herein. Representative examples include, but are not limited to methoxy, ethoxy, propoxy, butoxy, cyclohexyloxy.

"Alkoxycarbonyl" refers to a radical —C(O)-alkoxy where alkoxy is as defined herein.

"Alkoxycarbonylalkoxy" refers to a radical —OCR'R"C(O)-alkoxy where alkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_3$, —OCH$_2$C(O)OCH$_2$CH$_3$, —OCH(CH$_3$)C(O)OCH$_2$CH$_3$, —OCH(C$_6$H$_5$)C(O)OCH$_2$CH$_3$, —OCH(CH$_2$C$_6$H$_5$)C(O)OCH$_2$CH$_3$, —OC(CH$_3$)(CH$_3$)C(O)OCH$_2$CH$_3$.

"Alkoxycarbonylalkylamino" refers to a radical —NRCR'R"C(O)-alkoxy where alkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_3$, —N(CH$_3$)CH$_2$C(O)OCH$_2$CH$_3$, —NHCH(CH$_3$)C(O)OCH$_2$CH$_3$, —NHCH(C$_6$H$_5$)C(O)OCH$_2$CH$_3$, —NHCH(CH$_2$C$_6$H$_5$)C(O)OCH$_2$CH$_3$, and —NHC(CH$_3$)(CH$_3$)C(O)OCH$_2$CH$_3$.

"Alkylsulfonyl" refers to a radical —S(O)$_2$R where R is an alkyl, or cycloalkyl group as defined herein that may be optionally substituted by one or more substituents as defined herein. Representative examples include, but are not limited to, methylsulfonyl, ethylsulfonyl, propylsulfonyl, and butylsulfonyl.

"Alkylsulfinyl" refers to a radical —S(O)R where R is an alkyl, or cycloalkyl group as defined herein that may be optionally substituted by one or more substituents as defined herein. Representative examples include, but are not limited to, methylsulfinyl, ethylsulfinyl, propylsulfinyl, and butylsulfinyl.

"Alkylthio" refers to a radical —SR where R is an alkyl or cycloalkyl group as defined herein that may be optionally substituted by one or more substituents as defined herein.

Representative examples include, but are not limited to methylthio, ethylthio, propylthio, and butylthio.

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorine, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleidene, pyrene, pyranthrene, rubicene, triphenylene, trinaphthalene. Preferable, an aryl group comprises from 6 to 20 carbon atoms, more preferably, between 6 to 12 carbon atoms.

"Arylalkyl" refers to an acyclic alkyl in which one of the hydrogen atoms bonded to a carbon atom, typically a terminal or $sp^3$ carbon atom, is replaced with an aryl group. Typically arylalkyl groups include, but not limited to, benzyl, 2-phenylethan-1-yl, 2-phenylethen-1-yl, naphthylmethyl, 2-naphthylethan-1-yl, 2-naphthylethene-1-yl, naphthobenzyl, 2-naphthophenylethan-1-yl. Where specific alkyl moieties are intended, the nomenclature arylalkany, arylalkenyl and/or arylalkynyl is used. Preferably, an arylalkyl group is $(C_6-C_{30})$arylalkyl, e.g., the alkanyl, alkenyl or alkynyl moiety of the arylalkyl group is $(C_1-C_{10})$ and the aryl moiety is $(C_6-C_{20})$, more preferably, an arylalkyl group is $(C_6-C_{20})$ arylalkyl, e.g., the alkanyl, alkenyl or alkynyl moiety of the arylalkyl group is $(C_1-C_8)$ and the aryl moiety is $(C_6-C_{12})$.

"Arylalkoxy" refers to an —O-arylalkyl radical where arylalkyl is as defined herein that may be optionally substituted by one or more substituents as defined herein.

"Arylalkoxycarbonylalkoxy" refers to a radical —OCR'R'C(O)-arylalkoxy where arylalkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_2$C$_6$H$_5$, —OCH(CH$_3$)C(O)OCH$_2$C$_6$H$_5$, —OCH(C$_6$H$_5$)C(O)OCH$_2$C$_6$H$_5$, —OCH(CH$_2$C$_6$H$_5$)C(O)O CH$_2$C$_6$H$_5$, —OC(CH$_3$)(CH$_3$)C(O)OCH$_2$C$_6$H$_5$.

"Arylalkoxycarbonylalkylamino" refers to a radical —NRCR'R"C(O)-arylalkoxy where arylalkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_2$C$_6$H$_5$, —N(CH$_3$)CH$_2$C(O)OCH$_2$C$_6$H$_5$, —NHCH(CH$_3$)C(O)OCH$_2$C$_6$H$_5$, —NHCH(C$_6$H$_5$)C(O)OCH$_2$C$_6$H$_5$, —NHCH(CH$_2$C$_6$H$_5$)C(O)OCH$_2$C$_6$H$_5$, —NHC(CH$_3$)(CH$_3$)C(O)OCH$_2$C$_6$H$_5$.

"Aryloxycarbonyl" refers to radical —C(O)—O-aryl where aryl is defined herein that may be optionally substituted by one or more substituents as defined herein.

"Aryloxycarbonylalkoxy" refers to a radical —OCR'R"C(O)-aryloxy where aryloxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OC$_6$H$_5$, —OCH(CH$_3$)C(O)OC$_6$H$_5$, —OCH(C$_6$H)C(O)OC$_6$H$_5$, —OCH(CH$_2$C$_6$H)C(O)OC$_6$H$_5$, —OC(CH$_3$)(CH$_3$)C(O)OC$_6$H$_5$.

"Aryloxycarbonylalkylamino" refers to a radical —NRCR'R"C(O)-aryloxy where aryloxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OC$_6$H$_5$, —N(CH$_3$)CH$_2$C(O)OC$_6$H$_5$, —NHCH(CH$_3$)C(O)OC$_6$H$_5$, —NHCH(C$_6$H$_5$)C(O)OC$_6$H$_5$, —NHCH(CH$_2$C$_6$H$_5$)C(O)OC$_6$H$_5$, —NHC(CH$_3$)(CH$_3$)C(O)OC$_6$H$_5$.

"Carbamoyl" refers to the radical —C(O)NRR where each R group is independently, hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Carbamate" refers to a radical —NR'C(O)OR", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methylcarbamate (—NHC(O)OCH$_3$), ethylcarbamate (—NHC(O)OCH$_2$CH$_3$), benzylcarbamate (—NHC(O)OCH$_2$C$_6$H$_5$).

"Carbonate" refers to a radical —OC(O)OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methyl carbonate (—C(O)OCH$_3$), cyclohexyl carbonate (—C(O)OC$_6$H), phenyl carbonate (—C(O)OC$_6$H$_5$), benzyl carbonate (—C(O)OCH$_2$C$_6$H$_5$).

"Dialkylamino" means a radical —NRR' where R and R' independently represent an alkyl or cycloalkyl group as defined herein that may be optionally substituted by one or more substituents as defined herein. Representative examples include, but are not limited to dimethylamino, methylethylamino, di-(1-methylethyl)amino, (cyclohexyl)(methyl)amino, (cyclohexyl)(ethyl)amino, (cyclohexyl)(propyl)amino.

"Halo" means fluoro, chloro, bromo, or iodo.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)OR where R is heteroaryl as defined that may be optionally substituted by one or more substituents as defined herein.

"Heteroarylalkyl" refers to an acyclic alkyl radical in which one of the hydrogen atoms bonded to a carbon atom, typically a terminal or sp3 carbon atom, is replaced with a heteroaryl group. Preferably, the heteroarylalkyl radical is a 6-30 carbon membered heteroarylalkyl, e.g., the alkanyl, alkenyl or alkynyl moiety of the heteroarylalkyl is 1-10 membered and the heteroaryl moiety is a 5-20 membered heteroaryl, more preferably, a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Isomer" refers to compounds of the present invention that possess asymmetric carbon atoms (optical centers) or double bonds, the racemates, diastereomers, enantiomers, geometric isomers, structural isomers and individual isomers are all intended to be encompassed within the scope of the present invention.

As used herein, the term "patient" encompasses mammal patients. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs.

"Pharmaceutically acceptable" means approved or approvable by a regulatory agency of the Federal or state government or listed in the U.S. Pharmacopoeia or other generally recognized pharmacopoeia for use in animals, and more particularly in humans.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, or formed with organic acids such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, laurylsulfuric acid, gluconic acid, glutamic acid, hydroxynaphthoic acid, salicylic acid, stearic acid, muconic acid; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, or N-methylglucamine.

"Pharmaceutically acceptable vehicle" refers to a diluent, adjuvant, excipient or carrier with which a compound of the invention is administered.

"Phosphate" refers to a radical —OP(O)(OR')(OR''), where R' and R'' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Phosphonate" refers to a radical —P(O)(OR')(OR''), where R' and R'' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Preventing" or "Prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Protecting group" refers to a group of atoms that when attached to a reactive group in a molecule masks, reduces or prevents that reactivity. Examples of protecting groups can be found in Green et al., "Protective Groups in Organic Chemistry", (Wiley, $2^{nd}$ ed. 1991) and Harrison et al., "Compendium of Synthetic Organic Methods", vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitroveratryloxycarbonyl ("NVOC"). Representative hydroxyl protecting groups include, but are not limited to, those where the hydroxyl group is either acylated or alkylated such as benzyl, and trialkylsilyl ethers and allyl ethers.

"Racemate" refers to an equimolar mixture of enantiomers of a chiral molecule.

"Spacer" refers to a $C_{1-6}$ alkylene in which one or more of the carbons of the $C_{1-6}$ alkylene can optionally be replaced with O, S, or $NR^6$, wherein $R^6$ can be H or $C_{1-6}$ alkyl. The $C_{1-6}$ alkylene is optionally substituted. In certain aspects, the $C_{1-6}$ alkylene is optionally substituted by acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide.

"Substituted" refers to a group in which one or more hydrogen atoms are each independently replaced with the same or different substituents(s). Typical substituents include, but are not limited to, —X, —$R^{54}$, —$O^-$, =O, —$OR^{54}$, —$SR^{54}$, —S$^-$, =S, —$NR^{54}R^{55}$, =$NR^{54}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2OR^{54}$, —$OS(O)_2O^{31}$, —$OS(O)_2R^{54}$, —$P(O)(O-)_2$, —$P(O)(OR^{14})(O^{31})$, —OP(O)($OR^{54}$)($OR^{55}$), —$C(O)R^{54}$, —$C(S)R^{54}$, —$C(O)OR^{54}$, —$C(O)NR^{54}R^{55}$, —$C(O)O^-$, —$C(S)OR^{54}$, —$NR^{56}C(O)NR^{54}R^{55}$, —$NR^{56}C(S)NR^{54}R^{55}$, —$NR^{57}C(NR^{56})NR^{54}R^{55}$, and —$C(NR^{56})NR^{54}R^{55}$, where each X is independently a halogen; each $R^{54}$, $R^{55}$, $R^{56}$ and $R^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl.

"Sulfate" refers to a radical —OS(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonamide" refers to a radical —S(O)(O)NR'R", where R' and R" are independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein or optionally R' and R" together with the atom to which they are both attached form a cycloheteroalkyl or substituted cycloheteroalkyl ring. Representative examples include but not limited to azetidinyl, pyrrolidinyl, piperidinyl, morpholinyl, 4-(NR''')-piperazinyl or imidazolyl group wherein said group may be optionally substituted by one or more substituents as defined herein. R''' is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonate" refers to a radical —S(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Thio" means the radical —SH.

"Treating" or "Treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically (e.g., stabilization of a discernible symptom), physiologically, (e.g., stabilization of a physical parameter), or both.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated, and can be determined by one of skill in the art without undue experimentation.

Compounds of the Invention

The present invention provides phenylcycloalkylmethylamine derivatives of Formula (I):

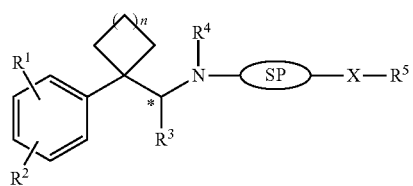

(I)

or isomer or pharmaceutically acceptable salt thereof, wherein:

n is 0, 1, 2, 3, 4, or 5; preferably n is 0 (cyclopropyl), 1 (cyclobutyl), 2 (cyclopentyl), or 3 (cyclohexyl), and more preferably n is 1.

SP is a spacer, wherein the spacer is $C_{1-6}$ alkylene, and wherein one or more of the carbons of the $C_{1-6}$ alkylene is optionally substituted with O, S, or $NR^6$, wherein $R^6$ is H or $C_{1-6}$ alkyl;

X is O, S, $NR^6$ or S(O)(O);

$R^1$, $R^2$, $R^3$, $R^4$, and $R^5$ are each independently hydrogen, $C_{1-6}$ alkyl, aryl, arylalkyl, cycloalkyl, cycloheteroalkyl, heteroaryl, heteroarylalkyl, acylalkyloxycarbonyl, acyloxyalkyloxycarbonyl, acylalkyloxycarbonylamino, acyloxyalkyloxycarbonylamino, $C_{1-6}$ alkoxy, alkoxycarbonyl, alkoxycarbonylalkoxy, alkoxycarbonylalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^1$, $R^2$, $R^3$, $R^4$, and $R^5$ is substituted with the isotopes $^2H$ (deuterium), $^3H$ (tritium), $^{13}C$, $^{15}N$, $^{17}O$, $^{18}O$, $^{18}F$, $^{31}P$, $^{32}P$, $^{35}S$, and $^{36}Cl$; and "*" denotes a carbon capable of being optically active.

The compounds of the present invention include (R)-isomers, (S)-isomers, and mixtures of (R)- and (S)-isomers. In one embodiment, the compounds are optically pure (R)-isomers, as they often are more active. In another embodiment, the compounds are optically pure (S)-isomers. Yet in another embodiment, the compounds are racemic compounds.

In one preferred embodiment, $R^1$ and $R^2$ are independently H, $C_{1-6}$ alkoxy (e.g., methoxy, ethoxy), halo (e.g., fluoro, chloro), or hydroxyl.

In one preferred embodiment, $R^3$ is H or $C_{1-6}$ alkyl (e.g., isobutyl).

In one preferred embodiment, $R^4$ is H.

In one preferred embodiment, SP is $C_{1-6}$alkylene.

In one preferred embodiment, $R^5$ is $C_{1-6}$ alkyl.

In one preferred embodiment, $R^6$ is $C_{1-6}$ alkyl.

The compounds of this invention described herein can have one or more of the following characteristics or properties:

1. Compounds of the invention can have dopamine transporter (DAT), norepinephrine transporter (NET) and serotonin transporter (SERT) inhibitory properties;
2. Oral bioavailability of the compounds is consistent with oral administration using standard pharmacological oral formulations; however, the compounds, and compositions thereof, can also be administered using any delivery system that produces constant and controllable blood levels over time.

In some embodiments, the subject invention provides compounds having any two or more of the above identified characteristics or properties. In a preferred embodiment the compounds of the invention have all four characteristics or properties.

Additional modifications of the compounds disclosed herein can readily be made by those skilled in the art. Thus, analogs and salts of the exemplified compounds are within the scope of the subject invention. With knowledge of the compounds of the subject invention skilled chemists can use known procedures to synthesize these compounds from available substrates. As used in this application, the term "derivatives" refers to compounds which are substantially the same as another compound but which may have been modified by, for example, adding additional side groups. The term "derivatives" as used in this application also may refer to compounds which are substantially the same as another compound but which have atomic or molecular substitution at certain locations in the compound.

The subject invention further pertains to enantiomerically isolated compounds, and compositions comprising the compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are at least about in 90%, 95%, 97%, or 99% enantiomeric excess.

Synthesis of the Compounds of the Invention

The compounds of the invention can be obtained via the synthetic methods illustrated in Schemes 1. Several methods have been described in the art for the synthesis of cycloalkylmethylamine analogs (see, e.g. U.S. Pat. No. 5,596,019; WO 2004/096202; WO 02/083631; WO 02/36540; WO 02/060424; Jeffery, J. E. et al., *J. Chem. Soc. Perkin Trans 1*, 1996, 2583-2589.). Other methods are known in the art for synthesizing cycloalkylmethylamines, which are readily accessible to the skilled artisan. The starting materials and intermediates used in the synthesis of target molecules (Scheme 1-8) thereof are commercially available or can be prepared by established procedures (See e.g., Green et al., "Protective Groups in Organic Synthesis," (Wiley, 4$^{rd}$ ed., 2006); Harrison et al "Compendium of Synthetic Organic Methods," vols. 1-8 (John Wiley and Sons, 1971-1996); "Beilstein Handbook of Organic Chemistry, Frankfurt, Germany; Feiser et al, "Reagents for Organic Synthesis," Volumes 1-45, Karger, 1991; March, Advanced Organic Chemistry," Wiley Interscience, 4$^{th}$ ed., 1992; Larock "Comprehensive Organic Transformations," Wiley-VCH Publishers, 2$^{nd}$ ed., 1999; Paquette, "Encyclopedia of Reagents for Organic Synthesis," John Wiley and Sons, 1$^{st}$ ed., 1995).

Accordingly, starting materials useful for preparing compounds of the invention and intermediates thereof are commercially available or can be prepared by well-known synthetic methods. Other methods for the synthesis of cycloalkylmethylamines described herein are either described in the art or will be readily apparent to the skilled artisan in view of the references provided above and may be used to synthesize the compounds of the invention. Accordingly, the methods presented in the Schemes herein are illustrative rather than comprehensive.

Methods

In one method, phenylcycloalkylmethylamine derivatives (7, 8) of Formula (I) are prepared as described in Scheme 2. The starting phenylcycloalkylamine building blocks (6) are prepared by modifying a reported procedure by Jeffery et al. (J. Chem. Soc., Perkin Trans. 1, 1996, 2583-2589) as illustrated in Scheme 1. The typical procedure involves reaction of a cycloalkylnitrile (3) with an appropriate Grignard reagent (R$^3$MgBr) in presence of toluene at a gentle reflux temperature for 10 to 24 hours followed by treating the intermediate with sodium borohydride in methanol or ethanol to get the corresponding cycloalkylmethylamine (6). The cycloalkylnitriles (3) used in the preparation of cycloalkylamines (6) are either purchased from Sigma-Aldrich or synthesized from the corresponding phenylacetonitriles (1) using standard chemistries. The selected racemic amines (6) are separated into corresponding optically pure (R)- and (S)-isomers by a standard chiral crystallization method using optically pure tartaric acid.

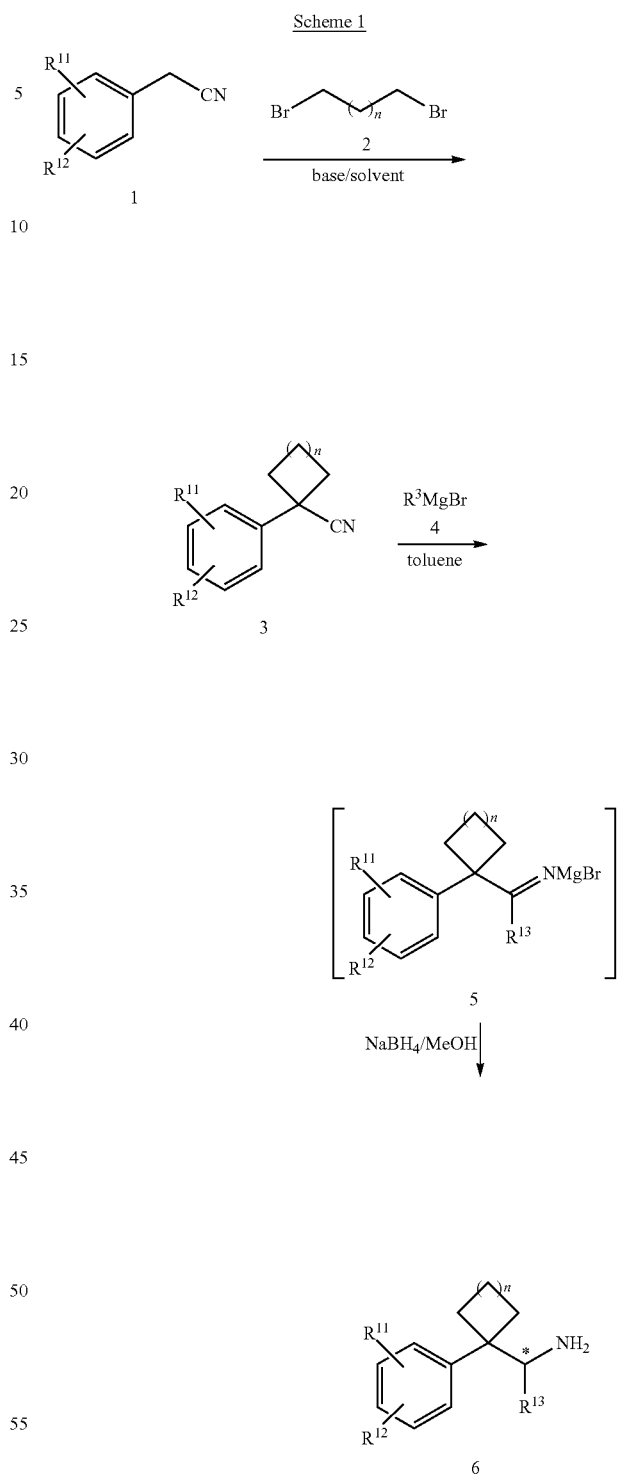

The phenylcycloalkylmethylamines (6) are alkylated with appropriate 4-nitrophenylsulfonyl esters (9) using cesium carbonate in N,N-dimethylformamide (DMF) solvent at room temperature to get the corresponding cycloalkylmethylamine ether derivatives (7, 8) in moderate to good yields as illustrated in scheme 2. The building blocks, 4-nitrophenylsulfonyl esters (9) are synthesized as illustrated in scheme 6.

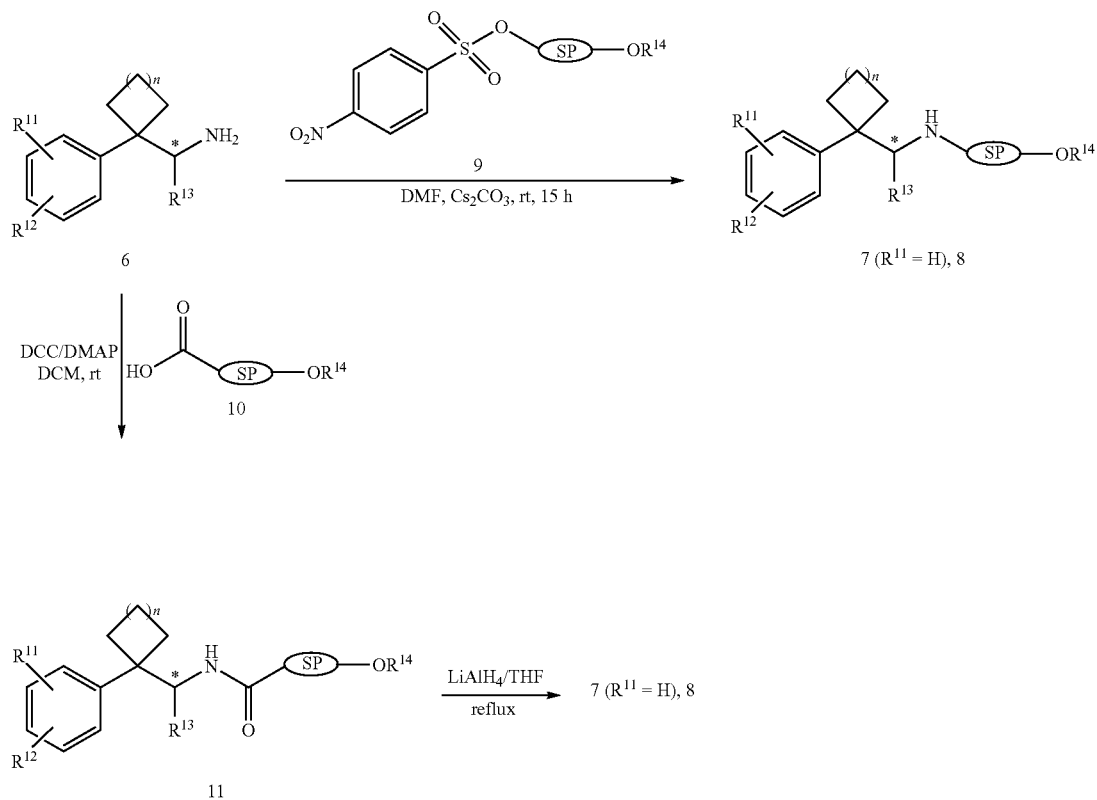

In another method, the phenylcycloalkylmethylamine ether derivatives (7, 8) are prepared by coupling with appropriate alkoxyalkylcarboxylic acids (10) followed by reduction of the amide intermediates (11) with lithium aluminum hydride (LAH) in anhydrous THF in moderate yields as illustrated in Scheme 2. The alkoxyalkylcarboxylic acids (10) are prepared as illustrated in scheme 7.

In another method, phenylcycloalkylmethylamine derivatives (12, 13) of Formula (I) are prepared as described in Scheme 3. The phenylcycloalkylamines (6) are coupled with appropriate alkylthioalkylcarboxylic acids (14) to get the amides (15) which after reduction with lithium aluminum hydride give the corresponding phenylcycloalkylmethylamine thioether derivatives (12, 13). The alkylthioalkylcarboxylic acids (14) are synthesized as illustrated in Scheme 8.

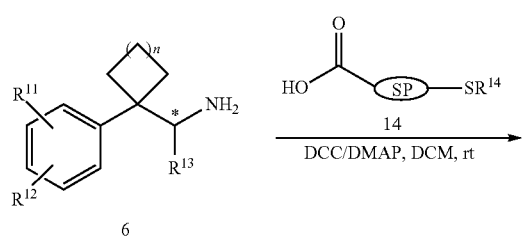

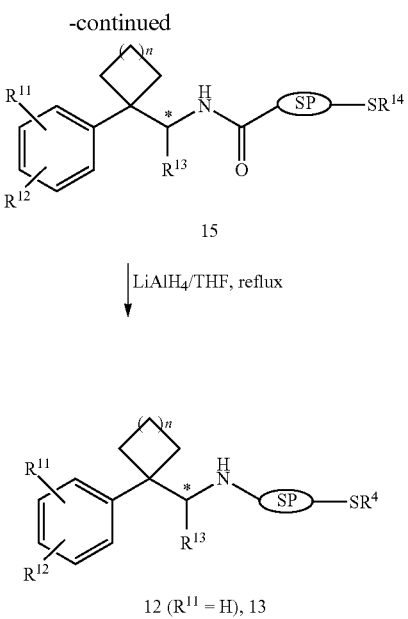

In another method phenylcycloalkylmethylamine derivatives (17) of Formula (I) are prepared as described in Scheme 4. The phenylcycloalkylamines (15) are oxidized using m-chloroperbenzoic acid (mCPBA) to get the amides (16) which after reduction with lithium aluminum hydride give the corresponding phenylcycloalkylmethylamine derivatives (17).

Scheme 4

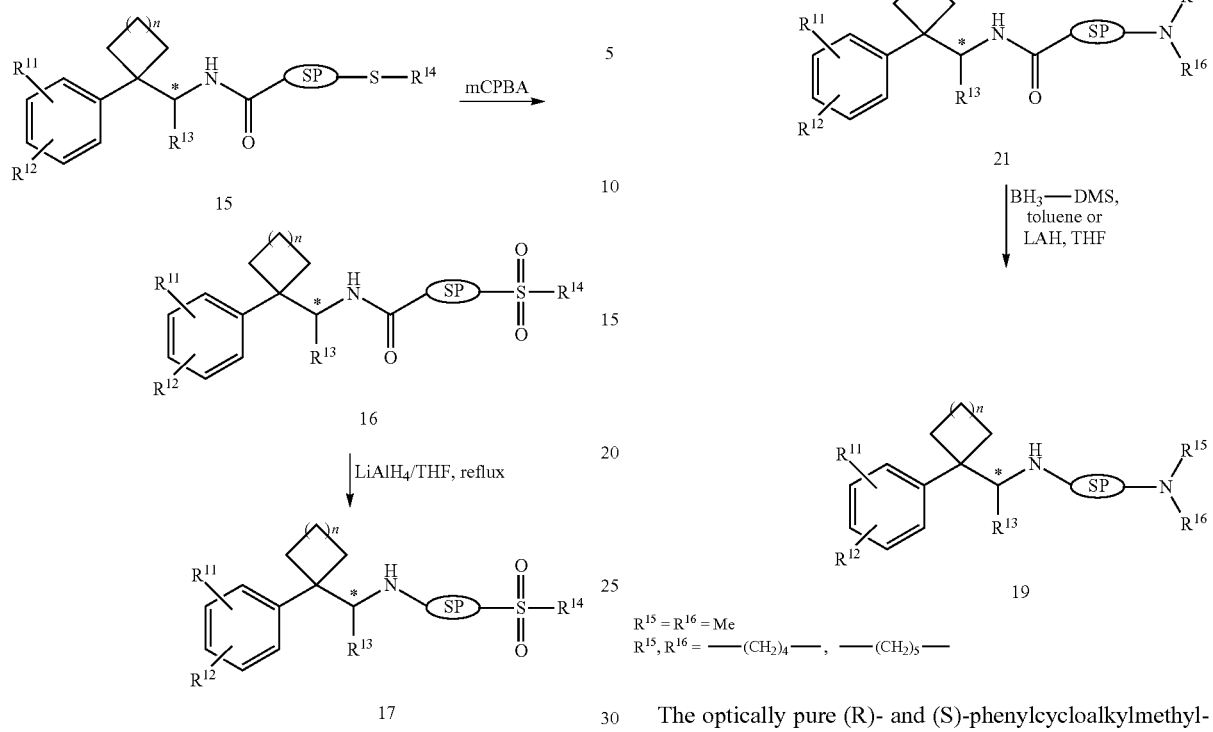

$R^{15} = R^{16} = Me$
$R^{15}, R^{16} = \text{—(CH}_2)_4\text{—}, \text{—(CH}_2)_5\text{—}$ In another method, phenylcycloalkylmethylamine derivatives (19) of Formula (I) are prepared as described in Scheme 5. The phenylcycloalkylamines (6) are coupled with appropriate alkylaminoalkylcarboxylic acid esters (20) in presence of trimethylaluminum in toluene to get the amides (21) which after reduction with borane-dimethylsulfide ($BH_3$-DMS) solution in toluene or LAH in THF give the corresponding phenylcycloalkylmethylamine derivatives (19).

Scheme 5

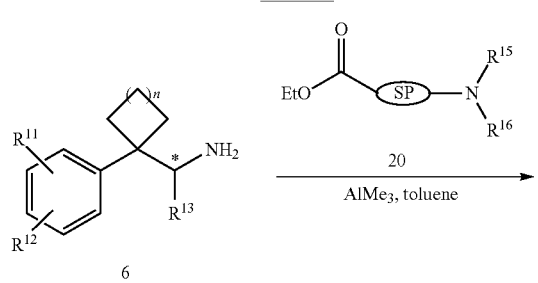

The optically pure (R)- and (S)-phenylcycloalkylmethylamine derivatives having Formula I are either prepared from the corresponding optically pure amines (6) or by subjecting the corresponding racemic phenylcycloalkylmethylamine derivatives (7, 8, 12, 13, 17 and 19) using chiral HPLC separation techniques. All phenylcycloalkylmethylamine derivatives (7, 8, 12, 13, 17 and 19) are converted into corresponding hydrochloride salts by treating with 2N HCl solution in ether under standard conditions.

The building blocks p-nitrophenylsulfonyl protected ethers (9) used in the synthesis of phenylcycloalkylmethylamine derivatives are synthesized in four steps as illustrated in scheme 6. The mono-benzyl protected diols (24) are synthesized by benzylating the corresponding diols (23) using sodium hydride as base in anhydrous tetrahydrofuran (THF) at 0° C. followed by refluxing the reaction mixture in good yields. The benzyl protected alcohols (24) are alkylated with appropriate alkyl halide using sodium hydride as base in anhydrous N,N-dimethylformamide (DMF) to get the ethers (25). The benzyl protecting group is cleaved under standard hydrogenation conditions to give the corresponding alcohol (26) which are reacted with p-nitrophenylsulfonylchloride using the mild base triethylamine in dichloromethane solvent to get the p-nitrophenylsulfonyl protected ethers (9) in overall good yields.

Scheme 6

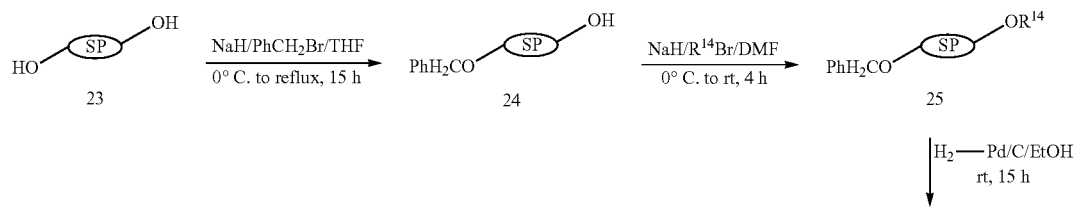

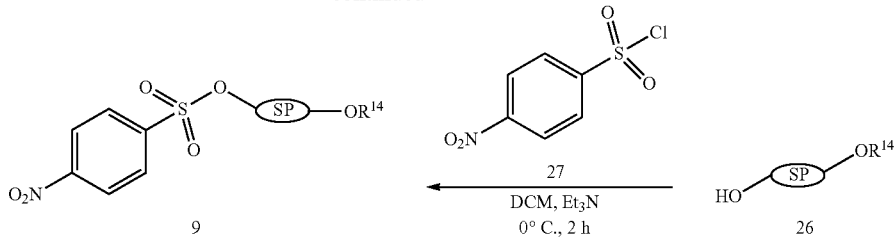

The starting building blocks 4-alkoxyalkylcarboxylic acid (10) is synthesized in two steps as illustrated in scheme 7. The gamma-butyrolactone (28) is reacted with ethylorthoformate (29) in the presence of ethanol and sulfuric acid to get the corresponding 4-ethoxybutyric acid ester (30) in good yields. The saponification of ester (30) under standard reaction conditions give the corresponding 4-ethoxybutyric acid (10) in good yield.

Scheme 7

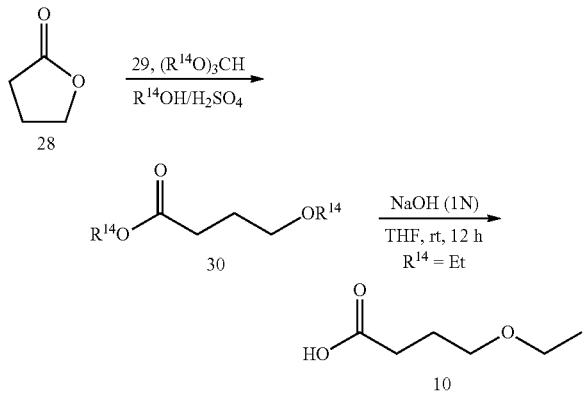

The starting building blocks alkylthioalkylcarboxylic acids (14) are synthesized in two steps as illustrated in scheme 8. The sodium thiolates (32) are alkylated with bromoalkylcarboxylic acids (31) in anhydrous DMF to get the esters (33) which after saponification give the corresponding alkylthioalkylcarboxylic acids (14).

Scheme 8

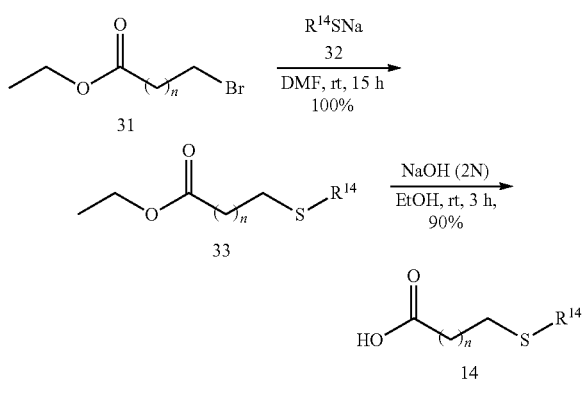

Therapeutic Uses of Compounds of Formula (I)

In various aspects, the present disclosure provides methods of treating or preventing obesity, depression, and associated co-morbid conditions in a patient. The method comprises administering to a patient in need of such treatment an effective amount of any one of the compounds of structural Formula (I). In further aspects, the method treats obesity, depression and related co-morbid symptom.

The present invention provides methods of treating and preventing obesity and associated co-morbid conditions. The term "co-morbid conditions associated with obesity" used in this document means medical conditions known to those skilled in the art to be associated with obesity. The term includes but not limited to the following: diabetes including non-insulin dependent diabetes mellitus, impaired glucose tolerance, hypertension, coronary thrombosis, stroke, depression, anxiety, psychoses (for example schizophrenia), tardive dyskinesia, drug addiction, drug abuse, cognitive disorders, Alzheimer's disease, cerebral ischaemia, obsessive-compulsive behavior, panic attacks, social phobias, eating disorders such as bulimia, anorexia, snacking and binge eating, lipid syndromes, hyperglycemia, hyperlipidemia, and stress in mammals particularly humans.

In addition, the compounds, compositions, and methods of the present invention can be used in the treatment or prevention of metabolic diseases and conditions arising therefrom, or for example non exercise activity thermogenesis and increased metabolic rate, sexual dysfunction, sleep apnoea, premenstrual syndrome, urinary incontinence including stress incontinence, hyperactivity disorders, hiatial hernia, and reflux esophagitis, pain, especially neuropathic pain, weight gain associated with drug treatment, chronic fatigue syndrome, osteoarthritis and gout, cancers associated with weight gain, menstrual dysfunction, gallstones, orthostatic hypotension and pulmonary hypertension.

The compounds, compositions, and methods of the present invention can be useful in preventing cardiovascular disease, and in reducing platelet adhesiveness, in aiding weight loss after pregnancy, reducing the craving to smoke and in aiding weight loss after smoking cessation. The present invention can also be useful in lowering uric acid levels and lipid levels in mammals particularly humans.

In accordance with the invention, a compound and/or a composition containing a compound of structural Formula (I) is administered to a patient, preferably a human, suffering from obesity and associated with co-morbid diseases and/or disorders. In certain embodiments, the compounds and/or compositions of the invention are administered to a patient, preferably a human, as a preventive measure against various diseases or disorders. Thus, the compounds and/or compositions containing compound(s) of structural Formula (I) may be administered as a preventive measure to a patient having a predisposition for obesity and associated co-morbid diseases and/or disorders (see WO 2004/058237; WO 2004/096202; WO 02/060424; WO 01/51453; WO 01/00205; WO 01/00187; Mueller, P. International Application Publication No. WO 00/32178; WO 98/11884; WO 98/13034).

Thus, those of skill in the art may readily assay and use the compounds and/or compositions containing compound(s) of Formulae (I) to treat obesity and associated co-morbid diseases and/or disorders.

Therapeutic/Prophylactic Administration

The compounds and/or compositions of the invention can be administered or applied singly, or in combination with other pharmaceutically active agents, to a patient.

The present compounds and/or compositions of the invention are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravabinal, transdermal, rectally, by inhalation, or topically, particularly to the ears, nose, eyes or skin.

In particularly, preferred embodiments, the compounds and/or compositions of the invention can be delivered via sustained release systems, preferably oral sustained release systems. In one embodiment, a pump may be used (see, Langer, supra; Sefton, 1987, CRC Crit. Ref Biomed. Eng. 14:201; Saudek et al., 1989, N. Engl. J. Med. 321:574).

In another embodiment, polymeric materials can be used (see "Medical Applications of Controlled Release," Langer and Wise (eds.), Wiley, New York (1984); Ranger and Peppas, 1983, J. Macromol. Sci. Rev. Macromol Chem. 23:61; see also Levy et al., 1985, Science 228:190; During et al., 1989, Ann. Neurol. 25:351; Howard et al, 1989, J. Neurosurg. 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (more preferred hydroxypropylmethylcellulose). Other preferred cellulose ethers have been described in the art (Bamba et al., Int. J. Pharm., 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time controlled release), polymers that are degraded by enzymes (i.e., enzyme controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm., 2000, 26:695-708). In a preferred embodiment, OROS® osmotic delivery systems (Alza Corporation, Mountain View, Calif.) are used for oral sustained release delivery devices (See for example, U.S. Pat. Nos. 3,845,770 and 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115-138 (1984)). Other controlled-release systems discussed in Langer, 1990, Science 249:1527-1533 may also be used.

The compounds, and/or compositions containing compound(s) of Formula (I) of the invention may be cleaved either chemically and/or enzymatically. One or more enzymes present in the stomach, intestinal lumen, intestinal tissue, blood, liver, brain or any other suitable tissue of a mammal may enzymatically cleave the compounds and/or compositions of the invention.

Compositions of the Invention

In various aspects, the present disclosure provides pharmaceutical compositions comprising any one of the compounds of structural Formula (I), and a pharmaceutically acceptable vehicle.

When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or pH buffering agents. In addition, auxiliary, stabilizing, thickening, lubricating and coloring agents may be used.

The pharmaceutical compositions may be manufactured by means of conventional mixing, dissolving, granulating, and emulsifying, encapsulating, entrapping or lyophilizing process. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, and capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles have been described in the art (see Remington's Pharmaceutical Sciences, Philadelphia College of Pharmacy and Science, $17^{th}$ Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents to provide a pharmaceutically palatable preparation. When in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as suspensions, elixirs and solutions, suitable carriers, excipients or diluents include water, saline, alkyleneglycols (e.g., propylene glycol), polyalkylene glycols (e.g., polyethylene glycol), oils, alcohols, slightly acidic buffers between pH 4 and pH 6 (e.g., acetate, citrate, ascorbate at between about 1 mM to about 50 mM) etc. Additionally, flavoring agents, preservatives, coloring agents, and bile salts may be added.

Compositions for administration via other routes may also be contemplated. For buccal administration, the compositions may take the form of tablets, lozenges, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as alcohol, glycol, polyglycol or fatty acid. Other methods of formulating liquid drug solutions or suspension suitable for use in aerosol devices are known to those of skill in the art (see, e.g., U.S. Pat. Nos. 5,112,598 and 5,556,611). A compound of the invention may also be formulated in rectal or vaginal compositions such as suppositories or retention enemas, e.g., containing conventional suppository bases such as cocoa, butter or other glycerides. In addition to the formulations described previously, a compound of the invention may also be formulated as depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

Methods of Use and Doses

The present invention provides methods of treating or preventing obesity in a patient, the method comprising administering to a patient in need of such treatment an effective amount of any one of the compounds of structural Formula (I).

The amount of a compound of the invention effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered is dependent on, among other factors, the subject being treated, and the weight of the subject, the severity of the affliction, the manner of administration and the judgment of the prescribing physician. For example, the dosage may be delivered in a pharmaceutical composition by a single administration, by multiple applications or controlled release. In a preferred embodiment, the compounds of the invention are delivered by oral sustained release administration. Preferably, in this embodiment, the compounds of the invention are administered twice per day (or preferably, once per day). Dosing may be repeated intermittently, may be provided alone or in combination with other drugs and may continue as long as required for effective treatment of the disease state or disorder.

The compounds of structural Formula (I) may be administered in the range 0.1-500 mg, preferably 1-100 mg per day, given in one or more doses, and more preferably 5 mg, 10 mg, 15 mg, 20 mg, 25 mg, 35 mg, or 50 mg per day, and most preferably 25 mg.

The compounds of the invention are preferably assayed in vitro and in vivo, for the desired therapeutic or prophylactic activity, prior to use in humans. The compounds of the invention may also be demonstrated to be effective and safe using animal model systems.

The therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. The dosage of a compound of the inventions described herein is within a range of circulating concentrations that include an effective dose with little or no toxicity.

The invention is further defined by reference to the following examples, which describe in detail preparation of compounds and compositions of the invention and assays for using compounds and compositions of the invention. It will be apparent to those skilled in the art that many modifications, both to materials and methods, may be practiced without departing from the scope of the invention.

EXAMPLES

In the examples below, the following abbreviations have the following meanings. If an abbreviation is not defined, it has its generally accepted meaning.

CDI=1,1'-Carbonyldiimidazole
DCM=dichloromethane
DMAP=4-N,N-dimethylaminopyridine
DMF=N,N-dimethylformamide
h=hours
HATU=O-(7-azabenzotriazol-1-yl)-N,N,N',N'-tetramethyluronium hexafluorophosphate
LC/MS=liquid chromatography/mass spectroscopy
M=molar
MTBE=methyl tert-butyl ether
rt=room temperature
TEA=triethylamine
THF=tetrahydrofuran
TFA=trifluoroacetic acid

General Procedure for Synthesis of Phenylcycloalkylmethylamine 6 (Scheme 1)

To a stirred solution of Grignard reagent (2M solution in ether, 0 065 mol) under nitrogen atmosphere was added drop wise a solution of phenylcycloalkylcarbonitrile (3) (0.026 mol) in 50 mL of toluene at 0° C. Then the reaction mixture was slowly heated at 92° C. for 18 h. The progress of the reaction was monitored by thin layer chromatography (TLC). The reaction mixture was cooled to room temperature and concentrated under reduced pressure. The residue was diluted with 30 mL of anhydrous methanol and cooled down at 0° C., and NaBH$_4$ (2.5 g) was added slowly portion wise. The resulting mixture was stirred until complete conversion of imine intermediate to the corresponding amine. After the reaction was completed, methanol was removed by evaporation. The residue was diluted with ethyl acetate, washed with saturated sodium bicarbonate, dried over MgSO$_4$ and evaporated under reduce pressure to give corresponding phenylcyclobutylmethylamine (6) which was purified by column chromatography on silica gel using a gradient of hexane and ethyl acetate. The pure products 6a-m gave satisfactory 1H NMR and/or Mass spectral data.

Example 1

3-Methyl-1-(1-(p-tolyl)cyclopropyl)butan-1-amine (6a)

Colorless oil (1.66 g, 61%). $^1$HNMR (400 MHz, CDCl$_3$): δ 0.65-0.70 (m, 3H); 0.77-0.80 (m, 1H); 0.85 (d, J=6.8 Hz, 6H); 0.98-1.11 (m, 2H); 1.22-1.30 (m, 2H); 1.70-1.77 (m, 1H); 2.10-1.13 (m, 1H); 2.28 (s, 3H); 7.09 (d, J=8.0 Hz, 2H); 7.20 (d, J=8.0 Hz, 2H). MS (ESI): m/z=218.20 (M+H$^+$).

Example 2

1-(1-(4-Chlorophenyl)cyclopropyl)-3-methylbutan-1-amine (6b)

Colorless oil (1.60 g, 60%). $^1$HNMR (400 MHz, CDCl$_3$): δ 0.65-0.70 (m, 3H); 0.77-0.80 (m, 1H); 0.85 (d, J=6.8 Hz, 6H); 0.87-1.01 (m, 1H); 1.18-1.27 (m, 3H); 1.69-1.73 (m, 1H); 2.16 (d, J=10.4 Hz, 1H); 7.23-7.24 (m, 4H). MS (ESI): m/z=238.20 (M+H$^+$).

Example 3

1-(1-(4-Florophenyl)cyclobutyl)-3-methylbutan-1-amine (6c)

Colorless oil (2.2 g, 70%). $^1$HNMR (400 MHz, CDCl$_3$): δ 0.58-0.65 (m, 1H); 0.84 (d, J=6.8 Hz, 3H); 0.88 (d, J=6.8 Hz, 3H); 1.15-1.21 (m, 1H); 1.67-1.70 (m, 1H); 1.80-1.86 (m, 1H); 1.93-1.98 (m, 1H); 2.12-2.18 (m, 1H); 2.28-2.37 (m, 3H); 2.97 (dd, J=2.0 Hz; 10.8 Hz, 1H); 6.93-7.08 (m, 3H); 7.12-7.16 (m, 1H).

Example 4

1-(1-(4-Chlorophenyl)cyclobutyl)-3-methylbutan-1-amine (6d)

Colorless oil (4.7 g, 72%). $^1$HNMR (400 MHz, CDCl$_3$): δ 0.84 (d, J=6.8 Hz, 3H); 0.88 (d, J=6.8 Hz, 3H); 1.13-1.23 (m, 2H); 1.66-1.68 (m, 1H); 1.79-1.84 (m, 1H); 1.90-1.96 (m, 1H); 2.15-2.16 (m, 1H); 2.25-2.33 (m, 3H); 2.98 (d, J=10.8 Hz, 1H); 7.06 (dd, J=1.6; 8.4 Hz, 2H); 7.24 (dd, J=1.6; 8.4 Hz, 2H).

Example 5

1-(1-(3,4-Dichlorophenyl)cyclobutyl)-3-methylbutan-1-amine (6e)

Colorless oil (3.6 g, 70%). $^1$HNMR (400 MHz, CDCl$_3$): δ 0.53-0.60 (m, 1H); 0.84 (d, J=6.8 Hz, 3H); 0.88 (d, J=6.8 Hz, 3H); 1.10-1.13 (m, 1H); 1.63-1.67 (m, 1H); 1.77-1.83 (m, 1H); 1.91-1.97 (m, 1H); 2.12-2.16 (m, 1H); 2.21-2.33 (m, 3H); 2.97 (d, J=10.8 Hz, 1H); 6.96 (dd, J=2.0 Hz; 8.4 Hz, 1H); 7.19 (d, J=2 Hz; 1H); 7.32 (d, J=8.4 Hz, 1H).

Example 6

1-(1-(2,4-Dichlorophenyl)cyclobutyl)-3-methylbutan-1-amine (6f)

Colorless oil (1.5 g, 72%). $^1$HNMR (400 MHz, CDCl$_3$): δ 0.84 (d, J=6.8 Hz, 3H); 0.88 (d, J=6.8 Hz, 3H); 1.13-1.15 (m, 1H); 1.23-1.26 (m, 1H) 1.71-1.81 (m, 2H); 1.92-2.03 (m, 1H); 2.35-2.43 (m, 4H); 3.24 (dd, J=2.0 Hz; 10.8 Hz, 1H); 7.02 (d, J=8.4 Hz, 1H); 7.16 (dd, J=2 Hz; 8.4 Hz, 1H); 7.29 (d, J=2.4 Hz, 1H).

Example 7

1-(1-(3,4-Dimethoxyphenyl)cyclobutyl)-3-methylbutan-1-amine (6g)

Colorless oil (3.6 g, 70%). $^1$HNMR (400 MHz, CDCl$_3$): δ 0.53-0.60 (m, 1H); 0.84 (d, J=6.8 Hz, 3H); 0.88 (d, J=6.8 Hz, 3H); 1.10-1.13 (m, 1H); 1.63-1.67 (m, 1H); 1.77-1.83 (m, 1H); 1.91-1.97 (m, 1H); 2.12-2.16 (m, 1H); 2.21-2.33 (m, 3H); 2.97 (d, J=10.8 Hz, 1H); 3.87 (s, 6H); 6.77-6.82 (m, 3H).

Example 8

1 1-(1-(4-Ethoxyphenyl)cyclobutyl)-3-methylbutan-1-amine (6h)

Colorless oil (1.06 g, 72%). $^1$HNMR (400 MHz, CDCl$_3$): δ 0.57-0.64 (m, 1H); 0.84 (d, J=6.8 Hz, 3H); 0.88 (d, J=6.8 Hz, 3H); 1.15-1.21 (m, 1H); 1.40 (t J=6.8 Hz, 3H); 1.67-1.69 (m, 1H); 1.79-1.84 (m, 1H); 1.90-1.96 (m, 1H); 2.14-2.16 (m, 1H); 2.27-2.36 (m, 3H); 2.98 (dd, J=2.0 Hz; 10.8 Hz, 1H); 4.02 (q, J=6.8 Hz, 2H); 6.83 (d, J=8.4 Hz, 2H); 7.05 (dd, J=8.4 Hz, 2H).

Example 9

3-Methyl-1-(1-(4-(methylthio)phenyl)cyclobutyl)butan-1-amine (6i)

Colorless oil (1.7 g, 34%). $^1$HNMR (400 MHz, CDCl$_3$): δ 0.56-0.62 (m, 1H); 0.83 (d, J=6.8 Hz, 3H); 0.88 (d, J=6.8 Hz, 3H); 1.04-1.06 (sbroad, 2H); 1.13-1.20 (m, 1H); 1.64-1.68 (m, 1H); 1.79-1.83 (m, 1H); 1.90-1.95 (m, 1H); 2.11-2.17 (m, 1H); 2.26-2.37 (m, 3H); 2.46 (s, 3H); 2.96 (d, J=10.8 Hz, 1H); 7.05 (d, J=8.4 Hz, 2H); 7.19 (d, J=8.4 Hz, 2H). MS (ESI): m/z=264.20 (M+H$^+$).

Example 10

3-Methyl-1-(1-(p-tolyl)cyclopentyl)butan-1-amine (6j)

Colorless oil (1.46 g, 60%). $^1$HNMR (400 MHz, CDCl$_3$): δ 0.68-0.78 (m, 1H); 0.83 (d, J=6.8 Hz, 6H); 0.99 (sbroad, 2H); 1.20-1.24 (m, 1H); 1.50-1.56 (m, 2H); 1.58-1.68 (m, 3H); 1.72-1.78 (m, 1H); 1.84-1.91 (m, 1H); 2.02-2.08 (m, 2H); 2.28 (s, 3H); 2.73 (d, J=10.8 Hz, 1H); 7.09 (d, J=8.0 Hz, 2H); 7.20 (d, J=8.0 Hz, 2H). MS (ESI): m/z=246.20 (M+H$^+$).

Example 11

1-(1-(4-Methoxyphenyl)cyclopentyl)-3-methylbutan-1-amine (6k)

Colorless oil (1.43 g, 55%). $^1$HNMR (400 MHz, CDCl$_3$): δ 0.66-0.77 (m, 2H); 0.81 (d, J=6.8 Hz, 6H); 0.97-1.02 (sbroad, 2H); 1.12-1.18 (m, 1H); 1.48-1.55 (m, 1H); 1.58-1.68 (m, 3H); 1.71-1.77 (m, 1H); 1.82-1.89 (m, 2H); 2.07-2.06 (m, 1H); 2.70 (d, J=10.8 Hz, 1H); 3.78 (s, 3H); 6.82 (d, J=8.8 Hz, 2H); 7.23 (d, J=8.8 Hz, 2H). MS (ESI): m/z=262.20 (M+H$^+$).

Example 12

3-Methyl-1-(1-(p-tolyl)cyclohexyl)butan-1-amine (6l)

Colorless oil (1.46 g, 60%). $^1$HNMR (400 MHz, CDCl$_3$): δ 0.63-0.76 (m, 1H); 0.77 (d, J=6.8 Hz, 3H); 0.83 (d, J=6.8 Hz, 3H); 1.17-1.32 (m, 5H); 1.37-1.66 (m, 6H); 2.24-2.36 (m, 4H); 2.52 (d, J=10.4 Hz, 1H); 7.09 (d, J=8.0 Hz, 2H); 7.20 (d, J=8.0 Hz, 2H). MS (ESI): m/z=260.20 (M+H$^+$).

Example 13

1-(1-(4-Chlorophenyl)cyclohexyl)-3-methylbutan-1-amine (6m)

Colorless oil (0.8 g, 32%). $^1$HNMR (400 MHz, CDCl$_3$): δ 0.60-0.66 (m, 1H); 0.75 (d, J=6.8 Hz, 3H); 0.81 (d, J=6.8 Hz, 3H); 0.95-1.00 (sbroad, 2H); 1.11-2.25 (m, 5H); 1.41-1.62 (m, 5H); 2.20-2.30 (m, 2H); 2.53 (d, J=10.8 Hz, 1H); 7.22 (d, J=8.8 Hz, 2H); 7.27 (d, J=8.8 Hz, 2H). MS (ESI): m/z=280.20 (M+H$^+$).

General Procedure for Synthesis of Phenylcyclobutylmethylamine Ether Derivatives 7 and 8 (Scheme 2)

To a stirred solution of cesium carbonate (1.4 g, 5.0 eq) in 10 mL of DMF was added appropriate phenylcyclobutylmethylamine (6) (0.0009 mol) and the resulting mixture was stirred at room temperature for 4 hrs. Then a solution suitable 4-nitrobenzenesulfonate (0.0045 mol. 5 eq) in 5 mL of DMF was added over a period of 5 minutes. The resulting mixture was stirred at rt temperature for overnight. The progress of the reaction was monitored by thin layer chromatography (TLC). The reaction mixture was filtered, diluted with 10 mL of ethyl acetate, washed with brine and dried over Na$_2$SO$_4$, evaporated to give the corresponding phenylcyclobutylmethylamine ether derivatives (7, 8) which were purified by silica gel column chromatography using a gradient of hexane and ethyl acetate. The pure products (7, 8) gave satisfactory 1H NMR and/or Mass spectral data. The selected racemic ether derivatives (7, 8) were subjected to chiral HPLC to get the corresponding optically pure (R)- and (S)-isomers. The chiral HPLC conditions: column—CHIRAL PAK IA 4.6×250 mm, 5 μM; mobile phase—0.1% DEA in hexane and ethanol; isocratic method with 0.8 ml per minute flow rate; injection volume 1.00 ul; and run time 20 min. All ether derivatives (7, 8) were converted in to the corresponding HCl salts by treating them with 1N HCl dioxane/water followed by lyophilization. The hydrochloride salts of ether derivatives (7, 8) were tested in monoamine transporters (MATs) in vitro pharmacology assays.

Example 14

1-(1-(4-Ethoxyphenyl)cyclobutyl)-N-(2-methoxyethyl)-3-methylbutan-1-amine (7a)

Colorless oil (100 mg, 28% yield). $^1$HNMR (400 MHz, CDCl$_3$): δ 0.57-0.66 (m, 1H); 0.83 (d, J=6.8 Hz, 3H); 0.88 (d, J=6.8 Hz, 3H); 1.08-1.12 (m, 1H); 1.41 (t, J=9.2 Hz, 3H); 1.59-1.68 (m, 1H); 1.71-1.89 (m, 2H); 2.16-2.38 (m, 4H); 2.73 (dbroad, J=3.2 Hz, 1H); 2.88 (t, J=6.8 Hz, 2H); 3.32 (s, 3H); 3.45 (t, J=7.2 Hz, 2H); 4.03 (q, J=7.2 Hz, 2H); 6.83 (d, J=8.4 Hz, 2H); 7.16 (d, J=8.4 Hz, 2H). MS (ESI): m/z=320.61 (M+H$^+$).

Example 15

N-(2-Ethoxyethyl)-1-(1-(4-ethoxyphenyl)cyclobutyl)-3-methylbutan-1-amine (7b)

Colorless oil (70 mg, 27% yield). $^1$HNMR (400 MHz, CDCl$_3$): δ 0.57-0.66 (m, 1H); 0.83 (d, J=6.8 Hz, 3H); 0.88 (d, J=6.8 Hz, 3H); 1.08-1.12 (m, 1H); 1.21 (t, J=9.6 Hz, 3H); 1.38-1.44 (m, 4H); 1.59-1.66 (m, 1H); 1.75-1.86 (m, 2H); 2.15-2.18 (m, 1H); 2.28-2.37 (m, 3H); 2.73 (dbroad, J=11.6 Hz, 1H); 2.73-2.92 (m, 2H); 3.43-3.50 (m, 3H); 4.03 (q, J=7.2 Hz, 2H); 6.83 (d, J=8.4 Hz, 2H); 7.16 (d, J=8.4 Hz, 2H). MS (ESI): m/z=334.72 (M+H$^+$).

Example 16

1-(1-(4-Ethoxyphenyl)cyclobutyl)-3-methyl-N-(2-propoxyethyl)butan-1-amine (7c)

Colorless oil (80 mg, 27% yield). $^1$HNMR (400 MHz, CDCl$_3$): δ 0.57-0.66 (m, 1H); 0.83 (d, J=6.8 Hz, 3H); 0.88 (d, J=6.8 Hz, 3H); 0.91-0.92 (m, 6H); 1.00-1.08 (m, 1H); 1.39-1.46 (m, 4H); 1.52-1.64 (m, 3H); 1.73-1.86 (m, 2H); 2.17-2.40 (m, 4H); 2.73 (sbroad, 1H); 2.88-2.94 (m, 2H); 3.36 (t, J=6.8 Hz, 2H); 3.48 (d, J=10.8 Hz, 2H); 4.03 (q, J=7.2 Hz, 2H); 6.83 (d, J=8.4 Hz, 7.16 (d, J=8.4 Hz, 1H). MS (ESI): m/z=348.40 (M+H$^+$).

Example 17

N-(2-Butoxyethyl)-1-(1-(4-ethoxyphenyl)cyclobutyl)-3-methylbutan-1-amine (7d)

Colorless oil (100 mg, 27% yield). $^1$HNMR (400 MHz, CDCl$_3$): δ 0.57-0.66 (m, 1H); 0.83 (d, J=6.8 Hz, 3H); 0.88 (d, J=6.8 Hz, 3H); 0.92 (t, J=9.6 Hz, 3H); 1.08-1.12 (m, 1H); 1.32-1.44 (m, 5H); 1.49-1.64 (m, 3H); 1.78-1.86 (m, 1H); 2.04-2.15 (m, 1H); 2.26-2.39 (m, 2H); 2.73 (dbroad, J=11.6 Hz, 1H); 2.86-2.91 (m, 2H); 3.38-3.48 (m, 4H); 3.64 (t, J=7.2H, 1H); 4.03 (q, J=7.2 Hz, 2H); 4.277 (t, J=6.8 Hz, 1H); 6.82 (d, J=8.4 Hz, 2H); 7.15 (d, J=8.4 Hz, 2H). MS (ESI): m/z=362.57 (M+H$^+$).

Example 18

1-(1-(4-Ethoxyphenyl)cyclobutyl)-N-(2-isobutoxyethyl)-3-methylbutan-1-amine (7e)

Colorless oil (90 mg, 27% yield). $^1$HNMR (400 MHz, CDCl$_3$): δ 0.57-0.66 (m, 1H); 0.83 (d, J=6.8 Hz, 3H); 0.88 (d, J=6.8 Hz, 3H); 0.90-1.04 (m, 6H); 1.08-1.12 (m, 1H); 1.38-1.44 (m, 4H); 1.60-1.68 (m, 1H); 1.70-1.91 (m, 3H); 2.13-2.20 (m, 1H); 2.27-2.42 (m, 3H); 2.71 (d, J=8.4 Hz, 1H); 2.85-2.92 (m, 2H); 3.17 (d, J=6.4 Hz, 2H); 3.58 (t, J=7.2H, 1H); 4.03 (q, J=7.2 Hz, 2H); 6.82 (d, J=8.4 Hz, 2H); 7.15 (d, J=8.4 Hz, 2H). MS (ESI): m/z=362.57 (M+H$^+$).

Example 19

N-(2-Ethoxyethyl)-3-methyl-1-(1-(4-(methylthio)phenyl)cyclobutyl)butan-1-amine (7f)

Colorless oil (0.20 g, 20%). $^1$HNMR (400 MHz, CDCl$_3$): δ 0.60-0.66 (m, 1H); 0.82 (d, J=6.8 Hz, 3H); 0.87 (d, J=6.8 Hz, 3H); 1.06-1.09 (m, 1H); 1.17 (t, J=7.2 Hz, 3H); 1.61-1.60 (m, 1H); 1.70-1.77 (m, 1H); 1.82-1.88 (1H); 2.14-2.19 (m, 3H); 2.23-2.29 (m, 2H); 2.35-2.41 (m, 1H); 2.46 (s, 3H); 2.72 (d, J=10 Hz, 1H); 2.88 (t, J=7.2H, 2H); 3.42-3.48 (m, 3H); 7.02 (d, J=8.8 Hz, 2H); 7.20 (d, J=8.8 Hz, 2H). MS (ESI): m/z=336.20 (M+H$^+$).

Example 20

N-(4-Ethoxybutyl)-3-methyl-1-(1-(4-(methylthio)phenyl)cyclobutyl)butan-1-amine (7g)

Colorless oil (0.21 g, 20%). $^1$HNMR (400 MHz, CDCl$_3$): δ 0.60-0.66 (m, 1H); 0.82 (d, J=6.8 Hz, 3H); 0.87 (d, J=6.8 Hz, 3H); 1.87 (t, J=7.2 Hz, 3H); 1.47-1.83 (m, 6H); 2.04-2.22 (m, 3H); 2.27-2.32 (m, 2H); 2.46 (s, 3H); 3.40-3.49 (m, 5H); 4.10-4.15 (m, 4H); 7.02 (d, J=8.8 Hz, 2H); 7.20 (d, J=8.8 Hz, 2H). MS (ESI): m/z=364.20 (M+H$^+$).

Example 21

1-(1-(4-Chlorophenyl)cyclobutyl)-N-(2-ethoxyethyl)-3-methylbutan-1-amine (7h)

$^1$HNMR (400 MHz, CDCl$_3$): δ 0.63-0.71 (m, 1H); 0.81 (d, J=6.8 Hz, 3H); 0.86 (d, J=6.8 Hz, 3H); 1.01-1.07 (m, 1H); 1.17 (t, J=7.2 Hz, 3H); 1.59-1.66 (m, 1H); 1.70-1.77 (m, 1H); 1.83-1.90 (m, 1H); 2.12-2.17 (m, 1H); 2.22-2.29 (m, 2H); 2.36-2.43 (m, 1H); 2.73 (dd, J=2.4 Hz; 10.0 Hz, 1H); 2.88 (t, J=5.6 Hz, 2H); 3.43-3.48 (m, 4H); 7.16 (d J=8.4 Hz, 2H); 7.23 (d, J=8.4 Hz, 2H). MS (ESI): m/z=325.10 (M+H$^+$).

Example 22

N-(2-Ethoxyethyl)-1-(1-(4-fluorophenyl)cyclobutyl)-3-methylbutan-1-amine (7i)

$^1$HNMR (400 MHz, CDCl$_3$): δ 0.64-0.71 (m, 1H); 0.82 (d, J=6.8 Hz, 3H); 0.86 (d, J=6.8 Hz, 3H); 1.02-1.08 (m, 1H); 1.17 (t, J=7.2 Hz, 3H); 1.59-1.66 (m, 1H); 1.70-1.78 (m, 1H); 1.83-1.92 (m, 1H); 2.12-2.17 (m, 2H); 2.21-2.31 (m, 2H); 2.36-2.43 (m, 1H); 2.72 (dd, J=2.4 Hz; 10.0 Hz, 1H); 2.88 (t, J=5.6 Hz, 2H); 3.43-3.44 (m, 4H); 6.95 (t, J=8.8 Hz, 2H); 7.18 (dd, J=5.2 Hz; 8.8 Hz, 2H). MS (ESI): m/z=308.67 (M+H$^+$).

Example 23

N-(2-Ethoxyethyl)-3-methyl-1-(1-(p-tolyl)cyclopropyl)butan-1-amine (7j)

Colorless oil (0.24 g, 22%). $^1$HNMR (400 MHz, CDCl$_3$): δ 0.46-0.50 (m, 1H); 0.67-0.72 (m, 1H); 0.75-0.79 (m, 1H); 0.80 (d, J=6.8 Hz, 3H); 0.83 (d, J=6.8 Hz, 3H); 1.04-1.13 (m, 1H); 1.16-1.20 (m, 4H); 1.23-1.31 (m, 1H); 1.70-1.76 (m, 1H); 1.94-1.98 (m, 1H); 2.30 (s, 3H); 2.75-2.80 (m, 1H); 3.21-3.27 (m, 1H); 3.45-3.54 (m, 4H); 7.06 (d, J=7.2 Hz, 2H); 7.20 (d, J=7.2 Hz, 2H). MS (ESI): m/z=290.20 (M+H$^+$).

Example 24

1-(1-(4-Chlorophenyl)cyclopropyl)-N-(2-ethoxyethyl)-3-methylbutan-1-amine (7k)

Colorless oil (0.22 g, 24%). $^1$HNMR (400 MHz, CDCl$_3$): δ 0.47-0.52 (m, 1H); 0.65-0.71 (m, 1H); 0.75-0.89 (m, 7H); 1.02-1.09 (m, 1H); 1.18 (t, J=7.2 Hz, 3H); 1.19-1.27 (m, 1H); 1.44 (sbroad, 2H); 1.68-1.73 (m, 1H); 1.95-1.98 (m, 1H); 2.73-2.79 (m, 1H); 3.17-3.23 (m, 1H); 3.47-3.53 (m, 2H); 7.06 (d, J=7.2 Hz, 2H); 7.17 (d, J=7.2 Hz, 2H). MS (ESI): m/z=310.20 (M+H$^+$).

Example 25

N-(2-Ethoxyethyl)-3-methyl-1-(1-(p-tolyl)cyclopentyl)butan-1-amine (7l)

Colorless oil (0.27 g, 22%). $^1$HNMR (400 MHz, CDCl$_3$): δ 0.60-0.75 (m, 1H); 0.75 (d, J=6.8 Hz, 3H); 0.78 (d, J=6.8 Hz, 3H); 1.06-1.21 (m, 1H); 1.18 (t, J=7.2 Hz, 3H); 1.26-1.47 (m, 3H); 1.57-1.65 (m, 3H); 1.72-1.80 (m, 1H); 1.84-2.00 (m, 3H); 2.34 (s, 3H); 2.54 (d, J=8.4 Hz, 1H); 2.78-2.85 (m, 1H); 2.86-2.90 (m, 1H); 3.15-3.49 (m, 4H); 6.81 (d, J=8.8 Hz, 2H); 7.26 (d, J=8.8 Hz, 2H). MS (ESI): m/z=317.20 (M+H$^+$).

Example 26

N-(2-Ethoxyethyl)-1-(1-(4-methoxyphenyl)cyclopentyl)-3-methylbutan-1-amine (7m)

Colorless oil (0.27 g, 22%). $^1$HNMR (400 MHz, CDCl$_3$): δ 0.60-0.75 (m, 1H); 0.75 (d, J=6.8 Hz, 3H); 0.78 (d, J=6.8 Hz, 3H); 1.06-1.21 (m, 1H); 1.18 (t, J=7.2 Hz, 3H); 1.26-1.47 (m, 3H); 1.57-1.65 (m, 3H); 1.72-1.80 (m, 1H); 1.84-2.00 (m, 3H); 2.51 (d, J=8.4 Hz, 1H); 2.78-2.85 (m, 1H); 2.86-2.90 (m, 1H); 3.15-3.45 (m, 4H); 3.77 (s, 3H); 6.81 (d, J=8.8 Hz, 2H); 7.26 (d, J=8.8 Hz, 2H). MS (ESI): m/z=334.20 (M+H$^+$).

Example 27

N-(4-ethoxybutyl)-3-methyl-1-(1-(p-tolyl)cyclohexyl)butan-1-amine (7n)

Colorless oil (0.18 g, 20%). $^1$HNMR (400 MHz, CDCl$_3$): δ 0.67-0.72 (m, 1H); 0.75 (d, J=6.8 Hz, 3H); 0.78 (d, J=6.8

Hz, 3H); 1.13-1.26 (m, 8H); 1.36-1.44 (m, 3H); 1.49-1.59 (m, 7H); 2.16 (d, J=12.8 Hz, 1H); 2.21-2.35 (m, 5H); 2.44-2.50 (m, 1H); 2.65-2.69 (m, 1H); 3.34-3.48 (m, 4H); 7.23 (d, J=8.8 Hz, 2H); 7.28 (d, J=8.8 Hz, 2H). MS (ESI): m/z=360.20 (M+H$^+$).

Example 28

1-(1-(4-Chlorophenyl)cyclohexyl)-N-(4-ethoxybutyl)-3-methylbutan-1-amine (7o)

Colorless oil (0.18 g, 20%). $^1$HNMR (400 MHz, CDCl$_3$): δ 0.58-0.65 (m, 1H); 0.75 (d, J=6.8 Hz, 3H); 0.78 (d, J=6.8 Hz, 3H); 1.07-1.13 (m, 1H); 1.56-1.26 (m, 6H); 1.38-1.63 (m, 10H); 2.13 (d, J=14.0 Hz, 1H); 2.21 (d, J=10 Hz, 1H); 2.28 (d, J=13.6 Hz, 1H); 2.45-2.51 (m, 1H); 2.68-2.74 (m, 1H); 3.36-3.48 (m, 4H); 7.23 (d, J=8.8 Hz, 2H); 7.28 (d, J=8.8 Hz, 2H). MS (ESI): m/z=381.20 (M+H$^+$).

Example 29

1-(1-(3,4-Dichlorophenyl)cyclobutyl)-N-(2-ethoxyethyl)-3-methylbutan-1-amine (8a)

Colorless oil (87 mg, 27% yield). $^1$HNMR (400 MHz, CDCl$_3$): δ 0.61-0.68 (m, 1H); 0.84 (d, J=6.8 Hz, 3H); 0.89 (d, J=6.8 Hz, 3H); 1.03-1.04 (m, 1H); 1.08 (t, J=7.2 Hz, 3H); 1.62-1.63 (m, 1H); 1.75-1.78 (m, 1H); 1.88-1.91 (m, 1H); 2.21-2.38 (m, 4H); 2.75 (dd, J=2.4 Hz; 10.0 Hz, 1H); 2.96-3.02 (m, 2H); 3.41 (q, J=7.2 Hz, 2H); 3.44 (t, J=4.4 Hz, 2H); 7.06 (dd, J=2.4 Hz; 8.4 Hz, 1H); 7.31 (d, J=2.0 Hz, 1H); 7.34 (d, J=8.4 Hz, 1H). MS (ESI): m/z=360.10 (M+H$^+$).

Example 30

(R)-1-(1-(3,4-Dichlorophenyl)cyclobutyl)-N-(2-methoxyethyl)-3-methylbutan-1-amine (8b)

Colorless oil (60 mg, 28% yield). $^1$HNMR (400 MHz, CDCl$_3$): δ 0.64-0.71 (m, 1H); 0.84 (d, J=6.8 Hz, 3H); 0.88 (d, J=6.8 Hz, 3H); 1.04 (t, J=12 Hz, 1H); 1.53 (sbroad, 1H); 1.62-1.65 (m, 1H); 1.73-1.81 (m, 1H); 1.88-1.91 (m, 1H); 2.15-2.25 (m, 3H); 2.37-2.44 (m, 1H); 2.74 (d, J=8.4 Hz, 1H); 2.75-2.94 (m, 2H); 2.96 (s, 3H). 3.44 (t, J=10.8 Hz, 2H); 7.06 (d, J=8.0 Hz, 1H); 7.33 (s, 1H); 7.34 (d, J=8.0 Hz, 1H). MS (ESI): m/z=346.03 (M+H$^+$).

Example 31

(S)-1-(1-(3,4-Dichlorophenyl)cyclobutyl)-N-(2-methoxyethyl)-3-methylbutan-1-amine (8c)

Colorless oil (100 mg, 27% yield). $^1$HNMR (400 MHz, CDCl$_3$): δ 0.64-0.71 (m, 1H); 0.84 (d, J=6.8 Hz, 3H); 0.88 (d, J=6.8 Hz, 3H); 1.04 (t, J=12 Hz, 1H); 1.53 (sbroad, 1H); 1.62-1.65 (m, 1H); 1.73-1.81 (m, 1H); 1.88-1.91 (m, 1H); 2.15-2.25 (m, 3H); 2.37-2.44 (m, 1H); 2.74 (d, J=8.4 Hz, 1H); 2.75-2.94 (m, 2H); 2.96 (s, 3H). 3.44 (t, J=10.8 Hz, 2H); 7.06 (d, J=8.0 Hz, 1H); 7.33 (s, 1H); 7.34 (d, J=8.0 Hz, 1H). MS (ESI): m/z=346.03 (M+H$^+$).

Example 32

(R)-1-(1-(3,4-Dichlorophenyl)cyclobutyl)-N-(3-propoxypropyl)-3-methylbutan 1-amine (8d)

Colorless oil (87 mg, 27% yield). $^1$HNMR (400 MHz, CDCl$_3$): δ 0.57-0.66 (m, 1H); 0.83 (d, J=6.8 Hz, 3H); 0.88 (d, J=6.8 Hz, 3H); 0.91 (t, J=9.6 Hz, 3H); 1.00-1.08 (m, 1H); 1.56-1.64 (m, 5H); 1.66-1.80 (m, 2H); 1.83-1.96 (m, 1H); 2.09-2.30 (m, 3H); 2.37-2.46 (m, 1H); 2.72-2.94 (m, 3H); 3.37 (t, J=10.8 Hz, 2H); 3.49 (t, J=10.8 Hz, 2H); 7.07 (dd, J=3.2 Hz, 11.2 Hz, 1H); 7.32 (s, 1H); 7.33 (d, J=8.4 Hz, 1H). MS (ESI): m/z=388.30 (M+H$^+$).

Example 33

(S)-1-(1-(3,4-Dichlorophenyl)cyclobutyl)-N-(3-propoxypropyl)-3-methylbutan-1-amine (8e)

Colorless oil (60 mg, 27% yield). $^1$HNMR (400 MHz, CDCl$_3$): δ 0.57-0.66 (m, 1H); 0.83 (d, J=6.8 Hz, 3H); 0.88 (d, J=6.8 Hz, 3H); 0.91 (t, J=9.6 Hz, 3H); 1.00-1.08 (m, 1H); 1.56-1.64 (m, 5H); 1.66-1.80 (m, 2H); 1.83-1.96 (m, 1H); 2.09-2.30 (m, 3H); 2.37-2.46 (m, 1H); 2.72-2.94 (m, 3H); 3.37 (t, J=10.8 Hz, 2H); 3.49 (t, J=10.8 Hz, 2H); 7.07 (dd, J=3.2 Hz, 11.2 Hz, 1H); 7.32 (s, 1H); 7.33 (d, J=8.4 Hz, 1H). MS (ESI): m/z=388.30 (M+H$^+$).

Example 34

(R)—N-(3-Butoxypropyl)-1-(1-(3,4-dichlorophenyl)cyclobutyl)-3-methylbutan-1-amine (8f)

Colorless oil (130 mg, 27% yield). $^1$HNMR (400 MHz, CDCl$_3$): δ 0.59-0.64 (m, 1H); 0.83 (d, J=6.8 Hz, 3H); 0.88 (d, J=6.8 Hz, 3H); 0.91 (t, J=9.6 Hz, 3H); 1.04-1.07 (m, 1H); 1.32-1.40 (m, 2H); 1.50-1.56 (m, 3H); 1.57-1.79 (m, 4H); 1.87-1.92 (m, 1H); 2.10-2.27 (m, 3H); 2.38-2.42 (m, 1H); 2.72-2.94 (m, 3H); 3.37 (t, J=10.8 Hz, 2H); 3.49 (t, J=10.8 Hz, 2H); 7.07 (dd, J=2.0 Hz, 8.0 Hz, 1H); 7.32 (s, 1H); 7.33 (d, J=8.0 Hz, 1H). MS (ESI): m/z=402.03 (M+H$^+$).

Example 35

(S)—N-(3-Butoxypropyl)-1-(1-(3,4-dichlorophenyl)cyclobutyl)-3-methylbutan-1-amine (8g)

Colorless oil (130 mg, 27% yield). $^1$HNMR (400 MHz, CDCl$_3$): δ 0.59-0.64 (m, 1H); 0.83 (d, J=6.8 Hz, 3H); 0.88 (d, J=6.8 Hz, 3H); 0.91 (t, J=9.6 Hz, 3H); 1.04-1.07 (m, 1H); 1.32-1.40 (m, 2H); 1.50-1.56 (m, 3H); 1.57-1.79 (m, 4H); 1.87-1.92 (m, 1H); 2.10-2.27 (m, 3H); 2.38-2.42 (m, 1H); 2.72-2.94 (m, 3H); 3.37 (t, J=10.8 Hz, 2H); 3.49 (t, J=10.8 Hz, 2H); 7.07 (dd, J=2.0 Hz, 8.0 Hz, 1H); 7.32 (s, 1H); 7.33 (d, J=8.0 Hz, 1H). MS (ESI): m/z=402.03 (M+H$^+$).

Example 36

(R)-1-(1-(3,4-Dichlorophenyl)cyclobutyl)-N-(4-methoxybutyl)-3-methylbutan-1-amine (8h)

Colorless oil (60 mg, 27% yield). $^1$HNMR (400 MHz, CDCl$_3$): δ 0.57-0.66 (m, 1H); 0.84 (d, J=8.8 Hz, 3H); 0.89 (d, J=8.8 Hz, 3H); 1.00-1.08 (m, 1H); 1.43-1.68 (m, 6H); 1.71-1.94 (m, 2H); 2.10-2.45 (m, 4H); 2.66-2.84 (m, 3H); 3.31 (s, 3H). 3.37 (t, J=10.8 Hz, 2H); 7.07 (dd, J=3.2 Hz, 11.6 Hz, 1H); 7.32 (s, 1H); 7.34 (d, J=11.6 Hz, 1H). MS (ESI): m/z=374.26 (M+H$^+$).

Example 37

(S)-1-(1-(3,4-Dichlorophenyl)cyclobutyl)-N-(4-methoxybutyl)-3-methylbutan-1-amine (8i)

Colorless oil (60 mg, 27% yield). $^1$HNMR (400 MHz, CDCl$_3$): δ 0.57-0.66 (m, 1H); 0.84 (d, J=8.8 Hz, 3H); 0.89

(d, J=8.8 Hz, 3H); 1.00-1.08 (m, 1H); 1.43-1.68 (m, 6H); 1.71-1.94 (m, 2H); 2.10-2.45 (m, 4H); 2.66-2.84 (m, 3H); 3.31 (s, 3H). 3.37 (t, J=10.8 Hz, 2H); 7.07 (dd, J=3.2 Hz, 11.6 Hz, 1H); 7.32 (s, 1H); 7.34 (d, J=11.6 Hz, 1H). MS (ESI): m/z=374.26 (M+H$^+$).

Example 38

(R)-1-(1-(3,4-Dichlorophenyl)cyclobutyl)-N-(4-ethoxybutyl)-3-methylbutan-1-amine (8j)

Colorless oil (100 mg, 27% yield). $^1$HNMR (400 MHz, CDCl$_3$): δ 0.57-0.66 (m, 1H); 0.84 (d, J=9.2 Hz, 3H); 0.89 (d, J=9.2 Hz, 3H); 1.01-1.08 (m, 1H); 1.20 (t, J=9.2 Hz, 3H); 1.43-1.64 (m, 6H); 1.71-1.94 (m, 2H); 2.09-2.41 (m, 4H); 2.66-2.84 (m, 3H); 3.40-3.51 (m, 4H). 7.08 (dd, J=2.8 Hz, 10.8 Hz, 1H); 7.32 (s, 1H); 7.34 (d, J=10.8 Hz, 1H). MS (ESI): m/z=388.26 (M+H$^+$).

Example 39

(S)-1-(1-(3,4-Dichlorophenyl)cyclobutyl)-N-(4-ethoxybutyl)-3-methylbutan-1-amine (8k)

Colorless oil (100 mg, 27% yield). $^1$HNMR (400 MHz, CDCl$_3$): δ 0.57-0.66 (m, 1H); 0.84 (d, J=9.2 Hz, 3H); 0.89 (d, J=9.2 Hz, 3H); 1.01-1.08 (m, 1H); 1.20 (t, J=9.2 Hz, 3H); 1.43-1.64 (m, 6H); 1.71-1.94 (m, 2H); 2.09-2.41 (m, 4H); 2.66-2.84 (m, 3H); 3.40-3.51 (m, 4H). 7.08 (dd, J=2.8 Hz, 10.8 Hz, 1H); 7.32 (s, 1H); 7.34 (d, J=10.8 Hz, 1H). MS (ESI): m/z=388.26 (M+H$^+$).

Example 40

1-(1-(3,4-Dichlorophenyl)cyclobutyl)-N-(4-isobutoxybutyl)-3-methylbutan-1-amine (8l)

Colorless oil (87 mg, 27% yield). $^1$HNMR (400 MHz, CDCl$_3$): δ 0.59-0.64 (m, 1H); 0.84 (d, J=9.2 Hz, 3H); 0.89 (d, J=9.2 Hz, 3H); 0.91 (sbroad, 6H); 1.01-1.07 (m, 1H); 1.45-1.63 (m, 6H); 1.66-1.92 (m, 3H); 2.10-2.31 (m, 2H); 2.37-2.49 (m, 2H); 2.68-2.82 (m, 3H); 3.16 (d, J=6.4 Hz, 2H); 3.40 (t, J=6.4H, 2H); 7.08 (dd, J=2.8 Hz, 10.8 Hz, 1H); 7.32 (s, 1H); 7.33 (d, J=10.8 Hz, 1H). MS (ESI): m/z=416.26 (M+H$^+$).

Example 41

1-(1-(3,4-Dichlorophenyl)cyclobutyl)-N-(2-ethoxyethyl)propan-1-amine (8n)

$^1$HNMR (400 MHz, CDCl$_3$): δ 0.69-0.74 (m, 1H); 0.89 (d, J=6.8 Hz, 3H); 1.19 (t, J=6.8 Hz, 3H); 1.39-1.47 (m, 1H); 1.71-1.78 (m, 1H); 1.86-1.96 (m, 1H); 2.17-2.27 (m, 3H); 2.36-2.43 (m, 1H); 2.54 (dd, J=2.4 Hz; 10.0 Hz, 1H); 2.79-2.85 (m, 1H); 2.88-2.94 (m, 1H); 3.43-3.49 (m, 4H); 7.06 (dd, J=2.4 Hz; 8.4 Hz, 1H); 7.30 (s, 1H); 7.32 (d, J=8.4 Hz, 1H). MS (ESI): m/z=332.60 (M+H$^+$).

Example 42

1-(1-(3,4-Dimethoxyphenyl)cyclobutyl)-N-(2-methoxyethyl)-3-methylbutan-1-amine (8o)

Colorless oil (100 mg, 27% yield). $^1$HNMR (400 MHz, CDCl$_3$): δ 0.72-0.78 (m, 1H); 0.84 (d, J=6.8 Hz, 3H); 0.88 (d, J=6.8 Hz, 3H); 1.06-1.12 (m, 1H); 1.60-1.68 (m, 1H); 1.77-1.91 (m, 2H); 2.13-2.20 (m, 1H); 2.28-2.40 (m, 3H); 2.72 (dbroad, J=9.2 Hz, 1H); 2.89 (t, J=5.6 Hz, 2H); 3.32 (s, 3H); 3.45 (t, J=7.2 Hz, 2H); 3.87 (s, 6H); 6.77-6.82 (m, 3H). MS (ESI): m/z=336.70 (M+H$^+$).

Example 43

1-(1-(3,4-Dimethoxyphenyl)cyclobutyl)-N-(2-ethoxyethyl)-3-methylbutan-1-amine (8p)

Colorless oil (88 mg, 27% yield). $^1$HNMR (400 MHz, CDCl$_3$): δ 0.72-0.78 (m, 1H); 0.84 (d, J=6.8 Hz, 3H); 0.88 (d, J=6.8 Hz, 3H); 1.06-1.12 (m, 1H); 1.18 (t, J=6.8 Hz, 3H); 1.52 (sbroad, 1H); 1.62-1.67 (m, 1H); 1.77-1.89 (m, 2H); 2.15-2.18 (m, 1H); 2.29-2.32 (m, 2H); 2.36-2.40 (m, 1H); 2.72 (dd, J=3.2 Hz; 6.8 Hz, 1H); 2.88 (t, J=1.6 Hz, 2H); 3.45-3.49 (m, 3H); 3.87 (s, 6H); 6.77-6.82 (m, 3H). MS (ESI): m/z=350.80 (M+H$^+$).

Example 44

1-(1-(3,4-Dimethoxyphenyl)cyclobutyl)-N-(3-methoxypropyl)-3-methylbutan-1-amine (8q)

Colorless oil (80 mg, 27% yield). $^1$HNMR (400 MHz, CDCl$_3$): δ 0.70-0.74 (m, 1H); 0.83 (d, J=6.8 Hz, 3H); 0.88 (d, J=6.8 Hz, 3H); 1.06-1.12 (m, 1H); 1.63-1.72 (m, 3H); 1.76-1.88 (m, 2H); 2.13-2.16 (m, 1H); 2.27-2.32 (m, 2H); 2.37-2.40 (m, 1H); 2.71 (dd, J=2.4 Hz; 9.6 Hz, 1H); 2.80-2.84 (m, 2H); 3.32 (s, 3H); 3.45 (t, J=6.4 Hz, 2H); 3.87 (s, 6H); 6.76-6.82 (m, 3H). MS (ESI): m/z=350.80 (M+H$^+$).

Example 45

1-(1-(3,4-Dimethoxyphenyl)cyclobutyl)-N-(3-ethoxypropyl)-3-methylbutan-1-amine (8r)

Colorless oil (100 mg, 27% yield). $^1$HNMR (400 MHz, CDCl$_3$): δ 0.70-0.74 (m, 1H); 0.83 (d, J=6.8 Hz, 3H); 0.88 (d, J=6.8 Hz, 3H); 1.08-1.12 (m, 1H); 1.19 (t, J=6.8 Hz, 3H); 1.63-1.72 (m, 3H); 1.76-1.88 (m, 2H); 2.13-2.16 (m, 1H); 2.27-2.32 (m, 2H); 2.37-2.40 (m, 1H); 2.71 (dd, J=2.4 Hz; 9.6 Hz, 1H); 2.82 (t, J=6.4 Hz, 2H); 3.43-3.50 (m, 4H); 3.87 (s, 6H); 6.76-6.82 (m, 3H). MS (ESI): m/z=364.62 (M+H$^+$).

Example 46

1-(1-(3,4-Dimethoxyphenyl)cyclobutyl)-N-(4-methoxybutyl)-3-methylbutan-1-amine (8s)

Colorless oil (130 mg, 27% yield). $^1$HNMR (400 MHz, CDCl$_3$): δ 0.70-0.74 (m, 1H); 0.83 (d, J=6.8 Hz, 3H); 0.88 (d, J=6.8 Hz, 3H); 1.08-1.12 (m, 1H); 1.57-1.64 (m, 6H); 1.78-1.89 (m, 3H); 2.13-2.16 (m, 1H); 2.27-2.32 (m, 2H); 2.37-2.40 (m, 1H); 2.74 (sbroad, 1H); 3.27 (sbroad, 3H); 3.36 (t, J=5.6 Hz, 2H); 3.87 (s, 6H); 6.76-6.82 (m, 3H). MS (ESI): m/z=364.62 (M+H$^+$).

Example 47

1-(1-(3,4-dimethoxyphenyl)cyclobutyl)-N-(4-ethoxybutyl)-3-methylbutan-1-amine (8t)

Colorless oil (100 mg, 27% yield). $^1$HNMR (400 MHz, CDCl$_3$): δ 0.69-0.74 (m, 1H); 0.83 (d, J=6.8 Hz, 3H); 0.88 (d, J=6.8 Hz, 3H); 1.04-1.12 (m, 1H); 1.19 (t, J=6.8 Hz, 3H); 1.24-1.30 (m, 3H); 1.45-1.51 (m, 2H); 1.58-1.65 (m, 2H);

2.14-2.18 (m, 1H); 2.27-2.40 (m, 3H); 2.69-2.78 (m, 3H); 3.39-3.42 (m, 4H); 3.87 (s, 6H); 6.76-6.82 (m, 3H). MS (ESI): m/z=378.20 (M+H$^+$).

General Procedure for Synthesis of Phenylcyclobutylmethylamine Thioether Derivatives 12 and 13 (Scheme 3)

To a stirred solution of phenylcycloalkylmethylamine (6) (1 eq), alkylthioalkylcarboxylic acid (14) (1.2 eq) and DMAP (0.6 g, 1 eq) in 20 mL of DCM at 0° C. under nitrogen atmosphere was added dropwise a solution of dicyclohexylcarbodiimide (DCC) (1.4 g., 0.0070 mol. 1.2eq) in 10 mL of DCM. After the addition was completed, the reaction mixture was stirred at room temperature for 15 h. The progress of the reaction was monitored by thin layer chromatography (TLC). The reaction mixture was filtered and the filtrate was concentrated under reduced pressure. The residue was purified by silica gel column chromatography to give the corresponding amides (15) as white color solid in 70-90% yield. To a suspension of lithium aluminum hydride (LAH) (0.417 g, 4.2eq) in 20 mL of THF anhydrous was added a solution of amide (15) (1 eq) in 20 mL of THF dropwise at 0° C. under nitrogen atmosphere. After the addition was complete, the reaction mixture was brought to rt and then to reflux for 24 h. The progress of the reaction was monitored by thin layer chromatography (TLC). The reaction mixture was cooled to 0° C. and quenched by adding 2.5 mL of water, followed by 4.5 mL 10% NaOH and finally 2 mL of water. After stirring for a while, ether was added. The mass was filtered through celite, washed with ethyl acetate. The combined filtrates was evaporated and the residue was purified by silica gel chromatography using a gradient of hexane and ethyl acetate as eluents to get the corresponding pure thioether derivatives (12, 13). The pure thioethers (12, 13) gave satisfactory 1H NMR and/or Mass spectral data. The selected racemic ether derivatives (12, 13) were subjected to chiral HPLC to get the corresponding optically pure (R)- and (S)-isomers using similar conditions described for ether derivatives (7,8) in scheme 2. All thioether derivatives (12, 13) were converted in to the corresponding HCl salts by treating them with 1N HCl dioxane/water followed by lyophilization. The hydrochloride salts of thioether derivatives (12, 13) were tested in monoamine transporters (MATs) in vitro pharmacology assays.

Example 48

N-(4-(Ethylthio)butyl)-1-(1-(4-fluorophenyl)cyclobutyl)-3-methylbutan-1-amine (12a)

Colorless oil (0.47g, 51% yield). $^1$HNMR (400 MHz, CDCl$_3$): δ 0.57-0.63 (m, 1H); 0.82 (d, J=6.8 Hz, 3H); 0.87 (d, J=6.8 Hz, 3H); 1.03-1.06 (m, 1H); 1.26 (t, J=7.2 Hz, 3H); 1.47-1.54 (m, 2H); 1.56-1.67 (m, 3H); 1.71-1.77 (m, 1H); 1.84-1.92 (m, 1H); 2.10-2.17 (m, 1H); 2.20-2.26 (m, 2H); 2.34-2.38 (m, 1H); 2.50-2.55 (m, 3H); 2.65-2.72 (m, 2H); 2.74-2.80 (m, 2H); 6.97 (dd, J=8.4 Hz; 11.6 Hz, 1H); 7.06 (dd, J=1.6 Hz; 7.6 Hz, 1H); 7.12-7.17 (m, 2H). MS (ESI): m/z=352.20 (M+H$^+$).

Example 49

1-(1-(4-Chlorophenyl)cyclobutyl)-N-(4-(ethylthio)butyl)-3-methylbutan-1-amine (12b)

Colorless oil (0.48g, 51% yield). $^1$HNMR (400 MHz, CDCl$_3$): δ 0.60-0.66 (m, 1H); 0.82 (d, J=6.8 Hz, 3H); 0.87 (d, J=6.8 Hz, 3H); 1.03-1.09 (m, 3H); 1.25 (t, J=7.2 Hz, 3H); 1.47-1.54 (m, 2H); 1.58-1.65 (m, 2H); 1.73-1.78 (m, 1H); 1.84-1.91 (m, 1H); 2.11-2.18 (m, 1H); 2.21-2.29 (m, 2H); 2.35-2.42 (m, 1H); 2.50-2.55 (m, 4H); 2.67-2.77 (m, 3H); 7.16 (d, J=8.8 Hz, 2H); 7.25 (d, J=8.8 Hz, 2H). MS (ESI): m/z=369.20 (M+H$^+$).

Example 50

1-(1-(4-Ethoxyphenyl)cyclobutyl)-N-(2-(ethylthio)ethyl)-3-methylbutan-1-amine (12c)

Colorless oil (0.37g, 52% yield)$^1$HNMR (400 MHz, CDCl$_3$): δ 0.69-0.75 (m, 1H); 0.82 (d, J=6.8 Hz, 3H); 0.87 (d, J=6.8 Hz, 3H); 1.05-1.11 (m, 1H); 1.26 (t, J=7.2 Hz, 3H); 1.40 (t J=7.2 Hz, 3H); 1.54-1.66 (m, 2H); 1.72-1.74 (m, 1H); 1.82-1.88 (m, 1H); 2.03-2.18 (m, 1H); 2.25-2.36 (m, 2H); 2.52 (q, J=7.6 Hz, 2H); 2.61 (t, J=6.8 Hz, 2H); 2.70 (dd, J=2.0 Hz; 9.6 Hz, 1H); 2.90 (t, J=6.8 Hz, 2H); 4.01 (q, J=7.2 Hz, 2H); 6.82 (d, J=8.4 Hz, 2H); 7.15 (d, J=8.4 Hz, 2H). MS (ESI): m/z=350.20 (M+H$^+$).

Example 51

4-(Butylthio)-N-(1-(1-(4-ethoxyphenyl)cyclobutyl)propyl)butan-1-amine (12d)

Colorless oil (0.47g, 53% yield)$^1$HNMR (400 MHz, CDCl$_3$): δ 0.72-0.80 (m, 1H); 0.84-0.91 (m, 6H); 1.34-1.46 (m, 6H); 1.48-1.65 (m, 6H); 1.71-1.80 (m, 1H); 1.82-1.89 (m, 1H); 2.15-2.37 (m, 4H); 2.46-2.51 (m, 5H); 2.63-2.75 (m, 2H); 4.01 (q, J=7.2 Hz, 2H); 6.82 (d, J=8.4 Hz, 2H); 7.15 (d, J=8.4 Hz, 2H). MS (ESI): m/z=378.20 (M+H$^+$).

Example 52

1-(1-(3,4-Dichlorophenyl)cyclobutyl)-N-(2-(ethylthio)ethyl)-3-methylbutan-1-amine (13a)

Colorless oil (0.41g, 53% yield). $^1$HNMR (400 MHz, CDCl$_3$): δ 0.60-0.67 (m, 1H); 0.82 (d, J=6.8 Hz, 3H); 0.87 (d, J=6.8 Hz, 3H); 1.03-1.06 (m, 2H); 1.26 (t, J=7.2 Hz, 3H); 1.55-1.61 (m, 1H); 1.70-1.74 (m, 1H); 1.80-1.86 (m, 1H); 2.08-2.14 (m, 1H); 2.18-2.23 (m, 2H); 2.30-2.35 (m, 1H); 2.43-2.50 (m, 2H); 2.53-2.60 (m, 2H); 2.68 (d, J=10.0 Hz, 1H); 2.81-2.91 (m, 2H); 7.04 (dd, J=2.0 Hz; 8.4 Hz, 1H); 7.30 (d, J=2.0H, 1H); 7.32 (d, J=8.4 Hz, 1H). MS (ESI): m/z=376.20 (M+H$^+$).

Example 53

N-(2-(Butylthio)ethyl)-1-(1-(3,4-dichlorophenyl)cyclobutyl)-3-methylbutan-1-amine (13b)

Colorless oil (0.27g, 50% yield). $^1$HNMR (400 MHz, CDCl$_3$): δ 0.60-0.67 (m, 1H); 0.81-0.92 (m, 9H); 1.04-1.10 (m, 1H); 1.34-1.45 (m, 2H); 1.50-1.58 (m, 2H); 1.60-1.65 (m, 1H); 1.73-1.78 (m, 1H); 1.85-1.91 (m, 1H); 2.15-2.19 (m, 1H); 2.23-2.30 (m, 2H); 2.35-2.40 (m, 1H); 2.46-2.50 (m, 2H); 2.58-2.62 (m, 2H); 2.68 (dd, J=2.4 Hz; 10.0 Hz, 1H); 2.85-2.93 (m, 2H); 7.04 (dd, J=2.0 Hz; 8.4 Hz, 1H); 7.30 (d, J=2.0H, 1H); 7.32 (d, J=8.4 Hz, 1H). MS (ESI): m/z=403.20 (M+H$^+$).

Example 54

1-(1-(3,4-Dichlorophenyl)cyclobutyl)-N-(4-(ethylthio)butyl)-3-methylbutan-1-amine (13c)

Colorless oil (0.37g, 52% yield). $^1$HNMR (400 MHz, CDCl$_3$): δ 0.57-0.63 (m, 1H); 0.82 (d, J=6.8 Hz, 3H); 0.87 (d, J=6.8 Hz, 3H); 1.03-1.06 (m, 1H); 1.26 (t, J=7.2 Hz, 3H); 1.47-1.54 (m, 2H); 1.56-1.67 (m, 3H); 1.71-1.77 (m, 1H); 1.84-1.92 (m, 1H); 2.10-2.17 (m, 1H); 2.20-2.26 (m, 2H); 2.34-2.38 (m, 1H); 2.50-2.55 (m, 3H); 2.65-2.72 (m, 2H); 2.74-2.80 (m, 2H); 7.04 (dd, J=2.0 Hz; 8.4 Hz, 1H); 7.30 (d, J=2.0H, 1H); 7.32 (d, J=8.4 Hz, 1H). MS (ESI): m/z=403.20 (M+H$^+$).

Example 55

N-(4-(Butylthio)butyl)-1-(1-(3,4-dichlorophenyl)cyclobutyl)-3-methylbutan-1-amine (13d)

Colorless oil (0.45g, 55% yield). $^1$HNMR (400 MHz, CDCl$_3$): δ 0.57-0.63 (m, 1H); 0.82 (d, J=6.8 Hz, 3H); 0.87 (d, J=6.8 Hz, 3H); 0.88 (t, J=7.2 Hz, 3H); 1.02-1.05 (m, 1H); 1.36-1.43 (m, 2H); 1.48-1.65 (m, 7H); 1.73-1.77 (m, 1H); 1.85-1.90 (m, 1H); 2.10-2.16 (m, 1H); 2.18-2.25 (m, 2H); 2.34-2.39 (m, 1H); 2.48-2.52 (m, 4H); 2.65-2.80 (m, 3H); 7.04 (dd, J=2.0 Hz; 8.4 Hz, 1H); 7.30 (d, J=2.0H, 1H); 7.32 (d, J=8.4 Hz, 1H). MS (ESI): m/z=431.20 (M+H$^+$).

Example 56

1-(1-(2,4-Dichlorophenyl)cyclobutyl)-N-(4-(ethylthio)butyl)-3-methylbutan-1-amine (13e)

Colorless oil (0.57g, 51% yield). $^1$HNMR (400 MHz, CDCl$_3$): δ 0.57-0.63 (m, 1H); 0.82 (d, J=6.8 Hz, 3H); 0.87 (d, J=6.8 Hz, 3H); 1.03-1.06 (m, 1H); 1.26 (t, J=7.2 Hz, 3H); 1.47-1.54 (m, 2H); 1.56-1.67 (m, 3H); 1.71-1.77 (m, 1H); 1.84-1.92 (m, 1H); 2.10-2.17 (m, 1H); 2.20-2.26 (m, 2H); 2.34-2.38 (m, 1H); 2.50-2.55 (m, 3H); 2.65-2.72 (m, 2H); 2.74-2.80 (m, 2H); 7.02 (d, J=8.4 Hz, 1H); 7.16 (dd, J=2 Hz; 8.4 Hz, 1H); 7.29 (d, J=2.4 Hz, 1H). MS (ESI): m/z=403.20 (M+H$^+$).

Example 57

1-(1-(3,4-dichlorophenyl)cyclobutyl)-N-(2-(ethylthio)ethyl)propan-1-amine (13f)

Colorless oil (0.27g, 52% yield). $^1$HNMR (400 MHz, CDCl$_3$): δ 0.72-0.79 (m, 1H); 0.92 (t, J=7.6 Hz, 3H); 1.23 (t, J=7.6 Hz, 3H); 1.42-1.48 (m, 1H); 1.72-1.79 (m, 1H); 1.86-1.93 (m, 1H); 2.18-2.30 (m, 3H); 2.34-2.41 (m, 1H); 2.49-2.55 (m, 3H); 2.60-2.69 (m, 2H); 2.80-2.89 (m, 1H); 2.86-2.97 (m, 1H); 7.04 (dd, J=2.0 Hz; 8.4 Hz, 1H); 7.30 (d, J=2.0H, 1H); 7.32 (d, J=8.4 Hz, 1H). MS (ESI): m/z=347.20 (M+H$^+$).

Example 58

4-(Butylthio)-N-(1-(1-(3,4-dichlorophenyl)cyclobutyl)propyl)butan-1-amine (13g)

Colorless oil (0.37g, 50% yield). $^1$HNMR (400 MHz, CDCl$_3$): δ 0.69-0.83 (m, 1H); 0.84-0.91 (m, 6H); 1.03-1.05 (m, 1H); 1.34-1.41 (m, 4H); 1.51-1.65 (m, 6H); 1.72-1.77 (m, 1H); 1.85-1.92 (m, 1H); 2.17-2.30 (m, 2H); 2.34-2.41 (m, 1H); 2.45-2.50 (m, 4H); 2.62-2.68 (m, 1H); 2.72-2.78 (m, 1H); 7.04 (dd, J=2.0 Hz; 8.4 Hz, 1H); 7.30 (d, J=2.0H, 1H); 7.32 (d, J=8.4 Hz, 1H). MS (ESI): m/z=403.20 (M+H$^+$).

General Procedure for Synthesis of Phenylcyclobutylmethylamine Alkylsulfonyl Derivatives 17 (Scheme 4)

Synthesis of Amide Derivatives (16, Step 1)

To a stirred solution of m-CPBA (m-chloroperbenzoic acid) (0.94 g, 2.1 eq) in 10 mL of THF was added at −30° C. (dry Ice/acetone) drop wise over 30 minutes a solution of amide (15) (0.0026 mol) in 10 mL of THF. The reaction progress was monitored by TLC. After the reaction was completed, 3 mL of triethylamine (TEA) was added followed by a solution of 10 mL saturated sodium bicarbonate. The organic layer was separated, washed with brine, dried over Na$_2$SO$_4$ and evaporated. The residue was purified by silica gel chromatography using a gradient of hexane and ethyl acetate as eluents to get the corresponding pure amides (16).

Synthesis of Alkylsulfonyl Derivatives (17, Step 2)

To a suspension of Lithium aluminum hydride (LAH) (0.3 g, 4.2eq) in 20 mL of THF anhydrous was added amide (16) (1 eq) in 10 mL of THF dropwise at 0° C. under nitrogen atmosphere. After the addition was complete, the reaction mixture was brought to room temperature and then to reflux for 15 h. The progress of the reaction was monitored by thin layer chromatography (TLC). The reaction mixture was cooled to 0° C. and quenched by adding 5 mL of water, followed by 9 mL 10% NaOH and finally 4 mL of water. After stirring for a while, ether was added. The mass was filtered through celite and washed with ethyl acetate. The combined filtrates were evaporated and the residue was purified by silica gel column chromatography using a gradient of hexane and ethyl acetate to get the corresponding sulfonyl derivatives (17). The pure sulfonyl derivatives (17) gave satisfactory 1H NMR and/or Mass spectral data. All sulfonyl derivatives (17) were converted in to the corresponding HCl salts by treating them with 1N HCl dioxane/water followed by lyophilization. The hydrochloride salts of alkylsulfonyl derivatives (17) were tested in monoamine transporters (MATs) in vitro pharmacology assays.

Example 59

N-(1-(1-(3,4-Dichlorophenyl)cyclobutyl)-3-methylbutyl)-4-(ethylsulfonyl)butanamide (16a)

Colorless oil (0.85g, 73% yield). $^1$HNMR (400 MHz, CDCl$_3$): δ 0.57-0.71 (m, 1H); 0.80 (d, J=6.8 Hz, 3H); 0.90 (d, J=6.8 Hz, 3H); 1.13-1.19 (m, 1H); 1.24 (t, J=7.2 Hz, 3H); 1.78-1.84 (m, 1H); 2.05-2.23 (m, 5H); 2.25-2.32 (m, 2H); 2.37-2.47 (m, 2H); 2.96-3.07 (m, 4H); 4.47-4.53 (m, 1H); 4.93 (d, J=10.4 Hz, 1H); 6.94 (dd, J=2.0 Hz; 8.4 Hz, 1H); 7.16 (d, J=2.0H, 1H); 7.38 (d, J=8.4 Hz, 1H). MS (ESI): m/z=449.20 (M+H$^+$).

Example 60

4-(butylsulfonyl)-N-(1-(1-(3,4-dichlorophenyl)cyclobutyl)-3-methylbutyl)butanamide (16b)

Colorless oil (0.85g, 73% yield). $^1$HNMR (400 MHz, CDCl$_3$): δ 0.57-0.71 (m, 1H); 0.80 (d, J=6.8 Hz, 3H); 0.91

(t, J=7.2 Hz, 3H); 0.95 (d, J=6.8 Hz, 3H); 1.13-1.19 (m, 1H); 1.38-1.50 (m, 3H) 1.75-1.85 (m, 3H); 2.05-2.23 (m, 5H); 2.25-2.32 (m, 2H); 2.37-2.47 (m, 2H); 2.93-2.97 (m, 2H); 3.01-3.05 (m, 2H); 4.47-4.53 (m, 1H); 4.93 (d, J=10.4 Hz, 1H); 6.94 (dd, J=2.0 Hz; 8.4 Hz, 1H); 7.16 (d, J=2.0H, 1H); 7.38 (d, J=8.4 Hz, 1H). MS (ESI): m/z=477.20 (M+H$^+$).

Example 61

1-(1-(3,4-Dichlorophenyl)cyclobutyl)-N-(4-(ethylsulfonyl)butyl)-3-methylbutan-1-amine (17a)

Colorless oil (0.11 g, 31% yield) $^1$HNMR (400 MHz, CDCl$_3$): δ 0.58-0.65 (m, 1H); 0.82 (d, J=6.8 Hz, 3H); 0.87 (d, J=6.8 Hz, 3H); 1.03-1.08 (m, 1H); 1.38 (t, J=7.2 Hz, 3H); 1.52-1.59 (m, 3H); 1.74-1.78 (m, 1H); 1.84-1.93 (m, 3H); 2.08-2.15 (m, 1H); 2.17-2.28 (m, 2H); 2.31-2.36 (m, 1H); 2.66-2.71 (m, 2H); 2.78-2.83 (m, 1H); 2.93-3.00 (m, 4H); 7.04 (dd, J=2.0 Hz; 8.4 Hz, 1H); 7.30 (d, J=2.0H, 1H); 7.32 (d, J=8.4 Hz, 1H). MS (ESI): m/z=435.20 (M+H$^+$).

Example 62

N-(4-(Butylsulfonyl)butyl)-1-(1-(3,4-dichlorophenyl)cyclobutyl)-3-methylbutan-1-amine (17b)

Colorless oil (0.07g, 37% yield) $^1$HNMR (400 MHz, CDCl$_3$): δ 0.59-0.65 (m, 1H); 0.82 (d, J=6.8 Hz, 3H); 0.87 (d, J=6.8 Hz, 3H); 0.95 (t, J=7.2 Hz, 3H); 1.03-1.05 (m, 1H); 1.43-1.51 (m, 2H); 1.52-1.62 (m, 3H); 1.72-1.86 (m, 4H); 1.88-1.93 (m, 3H); 2.08-2.38 (m, 4H); 2.66-2.71 (m, 2H); 2.78-2.84 (m, 1H); 2.91-2.97 (m, 4H); 7.04 (dd, J=2.0 Hz; 8.4 Hz, 1H); 7.30 (d, J=2.0H, 1H); 7.32 (d, J=8.4 Hz, 1H). MS (ESI): m/z=463.20 (M+H$^+$).

General Procedure for Synthesis of Phenylcycloalkylamine Derivatives 19 (Scheme 5)

Synthesis of Amides (21, Step 1)

To a stirred solution of trimethylaluminum 2 M solution (4 mL, 0.008 mol) in toluene was added dropwise a solution of phenylcycloalkylamine (6) (0.0053 mol, 1 eq) and ester (20) (0.0053 mol, 1 eq) in toluene under nitrogen atmosphere at 0° C. in a sealed tube. The reaction mixture was stirred at 80° C. for 5 h. The reaction progress was monitored by TLC. After completion of the reaction, the mixture was concentrated under vacuum, quenched with crushed ice and extracted with ethyl acetate (15 mL×3). The combined extract was dried over sodium sulfate and concentrated under reduced pressure. The residue was passed through a short column to get the pure amide (21). The amides (21a-d) were prepared according to this protocol. The starting esters (20) were prepared by alkylating the cyclic pyrrolidine and piperidine with appropriate bromoalkylcarboxylic acid esters under standard conditions using triethylamine (TEA) as a base in DCM as a solvent in good yields.

The amides (21e-f) were prepared by coupling 4-N,N-dimethylbutanoic acid with phenylcycloalkylamine (6) using HATU as a coupling agent. To a stirred solution of amine (6) (1 eq), 4-N,N-dimethylbutanoic acid (1 eq) and HATU (2 eq) solution in DCM was added dropwise a solution of N,N-diisopropylethylamine (DIEA) (3 eq) under nitrogen atmosphere at 0° C. The reaction mixture was stirred at room temperature for 5 h. The reaction progress was monitored by TLC. After completion of the reaction, the mixture was quenched with water and extracted with DCM, the combined extracts was dried over Na$_2$SO$_4$, and then evaporated under reduced pressure. The residue was purified by silica gel column chromatography using a gradient of DCM and methanol as eluents to get the pure amides (21e-f). The amides (21a-f) gave satisfactory 1H NMR and mass (LC/MS) mass data. As a representative example, the 1H NMR and mass data of amide (21d) is given herein.

Synthesis of Amines (19, Step 2)

Borane-DMS (1.5 eq) in THF was added dropwise to an ice cooled solution of amide (21) (1 eq) in THF. The reaction mixture was stirred at 60° C. for 3h. After completion of reaction, reaction mass was quenched with ice cooled water and then extracted twice with EtOAc. The combined organic layers were washed with brine and dried over Na$_2$SO$_4$. The organic layer was evaporated under reduced pressure. The crude product was in the form of amine-borane adduct or complex. The free base form of amine derivative (19) was obtained by treating the amine-borane complex according to the reported methods using Raney Nickel in methanol (Couturier, M. et al, Organic Letters, 2001, vol 3 (No. 3), 465-467) or piperazine in methanol (Zhou, Q. et al, Organic letters 2011, vol 13 (No. 3), 526-529). The crude free base form of amine derivatives (19) were purified by preparative HPLC using a gradient of hexane and ethanol as eluents to obtain the pure amine derivatives (19).

Example 63

N-(1-(1-(3,4-Dimethoxyphenyl)cyclobutyl)-3-methylbutyl)-4-(piperidin-1-yl)butanamide (21d)

Colorless oil (0.85g, 39% yield); $^1$HNMR (300 MHz, DMSOd$_6$): δ 0.73-0.76 (m, 6H); 0.85-0.98 (m, 2H); 1.39-1.59 (m, 8H); 1.71 (b, 3H); 1.83-1.89 (m, 2H); 2.11-2.17 (m, 6H); 2.27-2.49 (m, 4H); 3.73 (s, 3H); 3.74 (s, 3H); 4.19-4.25 (m, 1H), 6.62 (s, 1H); 6.64 (bs, 1H); 6.89 (d, J=7.8 Hz, 1H); 7.30 (bd, 1H, D$_2$O exchangeable); MS (ESI): m/z=431.17 (M+H$^+$).

Example 64

1-(1-(3,4-Dichlorophenyl)cyclobutyl)-3-methyl-N-(4-(pyrrolidin-1-yl)butyl)butan-1-amine (19a)

Colorless oil (0.092g, 18.7% yield); $^1$HNMR (300 MHz, DMSOd$_6$): δ 0.61-0.67 (m, 1H); 0.85 (d, J=7.2 Hz, 3H); 0.90 (d, J=6.4 Hz, 3H); 1.04-1.10 (m, 1H); 1.36-1.43 (m, 3H); 1.56-1.62 (m, 2H); 1.67-1.78 (m, 2H); 1.80-1.90 (m, 4H); 1.95-2.30 (m, 4H); 2.67-2.84 (m, 7H); 3.21 (bt, 2H); 7.07 (dd, J=2 Hz, 8 Hz, 1H), 7.31 (d, J=2 Hz, 1H); 7.34 (d, J=8.4 Hz, 1H); MS (ESI): m/z=411.16 (M+).

Example 65

1-(1-(3,4-Dimethoxyphenyl)cyclobutyl)-3-methyl-N-(4-(pyrrolidin-1-yl)butyl)butan-1-amine (19b)

Colorless oil (0.085g, 17.7% yield). $^1$HNMR (300 MHz, CDCl$_3$): δ 0.69-0.75 (m, 1H); 0.84 (d, J=6.6 Hz, 3H); 0.88 (d, J=6.6 Hz, 3H); 1.07-1.14 (m, 1H); 1.35-1.48 (m, 5H); 1.80-1.86 (m, 6H); 2.14-2.17 (m, 2H); 2.30-2.35 (m, 2H); 2.67-2.77 (m, 7H); 3.19 (bt, 2H); 3.87 (s, 6H); 6.79-6.81 (m, 3H); MS (ESI): m/z=403.23 (M+H$^+$).

Example 66

1-(1-(3,4-Dichlorophenyl)cyclobutyl)-3-methyl-N-(4-(piperidin-1-yl)butyl)butan-1-amine (19c)

Colorless oil (0.015g, 15.6% yield); $^1$HNMR (300 MHz, DMSOd$_6$): δ 0.59-0.62 (m, 1H); 0.79 (d, J=6.6 Hz, 3H); 0.84 (d, J=6.6 Hz, 3H); 0.94-1.02 (m, 1H); 1.33-1.38 (m, 2H); 1.46-1.48 (m, 3H); 1.59-1.75 (m, 8H); 2.11-2.16 (m, 2H); 2.43-2.50 (m, 2H); 2.65-2.77 (m, 9H); 7.20 (dd, J=5.1 Hz; 8.4 Hz, 1H); 7.42 (d, J=1.8 Hz, 1H); 7.51 (d, J=8.1 Hz, 1H). MS (ESI): m/z=425.13 (M+).

Example 67

1-(1-(3,4-Dimethoxyphenyl)cyclobutyl)-3-methyl-N-(4-(piperidin-1-yl)butyl)butan-1-amine (19d)

Colorless oil (0.060g, 15.5% yield). $^1$HNMR (400 MHz, CDCl$_3$): δ 0.61-0.67 (m, 1H); 0.85 (d, J=6.8 Hz, 3H); 0.97 (d, J=6.8 Hz, 3H); 1.07-1.14 (m, 1H); 1.22-1.28 (m, 2H); 1.33-1.47 (m, 3H); 1.58-1.71 (m, 2H); 1.61-1.67 (m, 2H); 1.73-2.30 (m, 6H); 2.35-2.42 (m, 1H); 2.67-2.84 (m, 8H); 3.23 (sbroad, 2H); 3.87 (s, 6H); 6.79-6.81 (m, 3H). MS (ESI): m/z=417.20 (M+H$^+$).

Example 68

N1-(1-(1-(3,4-dichlorophenyl)cyclobutyl)-3-methylbutyl)-N$^4$,N$^4$-dimethylbutane-1,4-diamine (19e)

Colorless oil (0.045g, 11.6% yield). $^1$HNMR (400 MHz, CDCl$_3$): δ 0.59-0.65 (m, 1H); 0.80 (d, J=6.8 Hz, 3H); 0.84 (d, J=6.8 Hz, 3H); 0.95-1.02 (m, 1H); 1.22-1.28 (m, 1H); 1.33-1.47 (m, 3H); 1.59-1.71 (m, 4H); 1.81-1.87 (m, 2H); 1.73-2.30 (m, 3H); 2.35-2.42 (m, 2H); 2.36-2.58 (m, 6H); 2.60-2.74 (m, 2H); 7.06 (dd, J=2.0 Hz; 8.4 Hz, 1H); 7.31 (d, J=2.0H, 1H); 7.35 (d, J=8.4 Hz, 1H). MS (ESI): m/z=386.20 (M+H$^+$).

Example 69

N1-(1-(1-(3,4-dimethoxyphenyl)cyclobutyl)-3-methylbutyl)-N$^4$,N$^4$-dimethylbutane-1,4-diamine (19f)

Colorless oil (0.08g, 20% yield). $^1$HNMR (400 MHz, CDCl$_3$): δ 0.59-0.65 (m, 1H); 0.80 (d, J=6.8 Hz, 3H); 0.84 (d, J=6.8 Hz, 3H); 0.95-1.02 (m, 1H); 1.22-1.28 (m, 1H); 1.33-1.47 (m, 3H); 1.59-1.71 (m, 4H); 1.81-1.87 (m, 2H); 1.73-2.30 (m, 3H); 2.35-2.42 (m, 2H); 2.36-2.58 (m, 6H); 2.60-2.74 (m, 2H); 3.87 (s, 6H); 6.79-6.81 (m, 3H). MS (ESI): m/z=377.20 (M+H$^+$).

General Procedure for Synthesis of Alkoxyalkyl 4-Nitrobenzenesulfonates 9 (Scheme 6)

Synthesis of Monobenzyloxy Carbinols (24, Step 1)

To a stirred suspension of NaH (3.5 g, 1.04eq) in dry THF (50 mL) was added diol (23) (3eq) over 0.5 h at 0° C. After the addition was complete, the mixture was brought to reflux and benzyl bromide (10 mL, 0.084 mol., 1 eq) was added dropwise. The reaction mixture was stirred at reflux for 12 h. The progress of the reaction was monitored by thin layer chromatography (TLC). After the reaction was complete, the mixture was allowed to cool to room temperature, and diluted with ether. The combined extracts were dried over MgSO$_4$, filtered, and concentrated under reduced pressure. The residue was passed through a short silica gel column using a gradient of hexane and ethyl acetate as eluents to get the pure monobenzyloxycarbinol (24) as a colorless oil in moderate yields.

Synthesis of Alkoxyalkylbenzyl Ethers (25, Step 2)

To a stirred suspension of NaH (0.75 g, 1.5eq) in dry DMF (20 mL) was added monobenzyloxycarbinol (24) (1 eq) in 10 mL of DMF at 0° C. After the addition was complete, the mixture was stirred for 1 h and then added dropwise a solution of appropriate alkyl bromide or iodide (2eq). The reaction mixture was stirred for 15 h and the progress of the reaction was monitored by thin layer chromatography (TLC). After completion of the reaction, the mixture was diluted with 25 mL water, extracted with ethyl acetate, dried over anhydrous MgSO$_4$, filtered, and concentrated under reduced pressure. The resulting oil was purified by silica gel column chromatography using a gradient of hexane and ethyl acetate as eluents to get the corresponding alkoxyalkyl benzyl ethers (25) as colorless oil.

Alkoxyalkylsulfonates (9, Step 3)

To a stirred suspension of Pd/C (10%)(activated)(0.8 g) in ethanol (10 mL) was added solution of alkoxyalkyl benzyl ether (25) (0.001 mol) in 10 mL of ethanol. The reaction mixture was kept under hydrogen pressure for 15 h. The progress of the reaction was monitored by thin layer chromatography (TLC). After the reaction was complete, the mixture was filtered through Celite, washed with ethyl acetate and the filtrate solution was concentrated under reduced pressure. The residue was passed through a short silica gel column using a gradient of hexane and diethyl ether as eluents to get the corresponding carbinolether (26) as colorless oil. The carbinolether (26) was treated with 4-nitrosulfonyl chloride in presence a mild base triethylamine (TEA) in DCM at 0° C. to 5° C. The progress of the reaction was monitored by TLC. After the reaction was complete, the mixture was washed with water, dried over anhydrous magnesium sulfate and concentrated under reduced pressure. The residue was purified by silica gel chromatography using a gradient of hexane and ethyl acetate as eluents to get the alkoxyalkylsulfonates (9).

Example 70

2-Ethoxyethyl 4-nitrobenzenesulfonate (9a)

White solid (1.87g, 93% yield). $^1$HNMR (400 MHz, CDCl$_3$): δ 1.08 (t, J=7.2 Hz, 3H); 3.41 (q, J=7.2 Hz, 2H); 3.61 (t, J=4.4 Hz, 2H); 4.28 (t, J=4.4 Hz, 2H); 8.16 (d, J=8.8 Hz, 2H); 8.37 (d, J=8.8 Hz, 2H).

Example 71

2-Methoxyethyl 4-nitrobenzenesulfonate (9b)

White solid (1.87g, 93% yield). $^1$HNMR (400 MHz, CDCl$_3$): δ 3.28 (s, 3H); 3.59 (t, J=4.4 Hz, 2H); 4.30 (t, J=4.4 Hz, 2H); 8.13 (d, J=8.8 Hz, 2H); 8.40 (d, J=8.8 Hz, 2H).

Example 72

2-Ethoxybutyl 4-nitrobenzenesulfonate (9c)

White solid (1.87g, 93% yield). $^1$HNMR (400 MHz, CDCl$_3$): δ 1.08 (t, J=6.8 Hz, 3H); 1.59-1.63 (m, 2H);

1.76-1.83 (m, 2H); 3.37-3.45 (m, 4H); 4.19 (t, J=6.4 Hz, 2H); 8.11 (d, J=8.8 Hz, 2H); 8.40 (d, J=8.8 Hz, 2H).

Example 73

2-Methoxybutyl 4-nitrobenzenesulfonate (9d)

White solid (1.87g, 93% yield). $^1$HNMR (400 MHz, CDCl$_3$): δ 1.57-1.63 (m, 2H); 1.72-1.82 (m, 2H); 3.28 (s, 3H); 3.33-3.44 (m, 3H); 4.10 (t, J=6.4 Hz, 2H); 8.11 (d, J=8.8 Hz, 2H); 8.40 (d, J=8.8 Hz, 2H).

Example 74

4-Propoxybutyl 4-nitrobenzenesulfonate (9e)

White solid (1.87g, 93% yield). $^1$HNMR (400 MHz, CDCl$_3$): δ 0.84 (t, J=7.2 Hz, 3H); 1.44-1.51 (m, 2H); 1.91-1.97 (m, 2H); 3.28 (t, J=6.8 Hz, 2H); 3.43 (t, J=, 5.6 Hz, 2H); 4.26 (t, J=6.4 Hz, 2H); 8.11 (d, J=8.8 Hz, 2H); 8.40 (d, J=8.8 Hz, 2H).

Example 75

4-Butoxypropyl 4-nitrobenzenesulfonate (9f)

White solid (1.87g, 93% yield). $^1$HNMR (400 MHz, CDCl$_3$): δ 0.88 (t, J=7.2 Hz, 3H); 1.25-1.31 (m, 2H); 1.41-1.47 (m, 2H); 1.94 (t, J=6.0 Hz, 2H); 3.31 (t, J=6.4 Hz, 2H); 3.42 (t, J=, 5.6 Hz, 2H); 4.26 (t, J=6.4 Hz, 2H); 8.11 (d, J=8.8 Hz, 2H); 8.40 (d, J=8.8 Hz, 2H).

Example 76

Ethyl 4-ethoxybutanoate (30) (Scheme 7)

Sulfuric acid 0.25 mL (0.0045 mmol, 0.035eq) was added to an ice cooled solution of γ-butyrolactone (28) (11.2 g, 0.13009 mmol, 1.0 eq), triethyl orthoformate (29) (41.1 mL, 0.2497 mmol., 1.92eq) in 100 mL of ethanol. The mixture was heated at 50° C. for 12 h while monitoring the reaction by TLC. The reaction mixture was cooled to room temperature and most of the solvent was evaporated under reduced pressure. The concentrated reaction mixture was quenched with cold saturated NaHCO$_3$ solution and extracted with ethyl acetate twice. The combined organic extracts was dried over anhydrous Na$_2$SO$_4$ and concentrated under vacuum to yielded 20 g (95%) of ethyl 4-ethoxybutanoate (30) as light yellow oil. $^1$HNMR (400 MHz, CDCl$_3$): δ 1.16-1.28 (m, 6H); 1.87-1.91 (m, 2H); 2.39 (t, J=9.6 Hz; 2H); 3.42-3.50 (m, 2H); 3.57-3.64 (m, 2H); 4.13 (q, J=6 Hz, 2H).

Example 77

4-Ethoxybutanoic Acid (10) (Scheme 7)

To an ice cold stirred solution of ethyl 4-ethoxybutanoate (30) (~1 g) in 10 mL of tetrahydrofuran (THF) was added aqueous NaOH solution (0.62 g in 7 ml of H$_2$O) and stirred at room temperature for 12 h, while monitoring the reaction by TLC. Most of the solvent was evaporated under reduced pressure and the residue was diluted with water (10 mL). The aqueous layer was acidified with 1N HCl solution (PH~2) and then extracted with ethyl acetate (15 mL×3). The combined organic extracts was dried over anhydrous Na$_2$SO$_4$ and concentrated under vacuum to yield 0.6 g (73.14) of 4-ethoxybutanoic acid as light yellow oil. $^1$HNMR (400 MHz, CDCl$_3$): δ 1.20 (t, J=9.2 Hz, 3H); 1.87-1.95 (m, 2H); 2.47 (t, J=10 Hz; 2H); 3.48 (q, J=9.2 Hz, 4H).

General Procedure for Synthesis of Alkylthioalkylcarboxylic Acid Esters (33) (Scheme 8)

To a stirred solution of sodium alkanethiolate (32) (1 eq) in anhydrous DMF (10 mL) at 0° C. was added bromoalkylcarboxylic acid ester (31) (1 eq) over 5 min. The reaction mixture was stirred for 15 h at room temperature. The progress of the reaction was monitored by thin layer chromatography (TLC). The reaction mixture was diluted with ethyl acetate (20 mL) and washed with saturated NaHCO$_3$ solution (the aqueous layer was quenched with bleach). The organic layer was dried over anhydrous Na$_2$SO$_4$ to give the corresponding alkylthioethercarboxylic acid ester (33) which was purified by silica gel column chromatography using a gradient of hexane and ethyl acetate and isolated as colorless oil

Example 78

Ethyl 4-(ethylthio)butanoate (33a)

Colorless oil (6.87g, 100% yield). $^1$HNMR (400 MHz, CDCl$_3$): δ 1.20-1.26 (m, 6H); 1.84-1.92 (m, 2H); 2.40 (t, J=9.6 Hz, 2H); 2.47-2.55 (m, 4H); 4.12 (q, J=7.2 Hz, 2H).

Example 79

Ethyl 2-(ethylthio)acetate (33b)

Colorless oil (5.87g, 90% yield). $^1$HNMR (400 MHz, CDCl$_3$): δ 1.20-1.29 (m, 6H); 2.63 (q, J=7.6 Hz, 2H); 3.19 (s, 2H); 4.15 (q, J=7.2 Hz, 2H).

Example 80

Ethyl 4-(butylthio)butanoate (33c)

Colorless oil (14.12g, 100% yield). $^1$HNMR (400 MHz, CDCl$_3$): δ 0.89 (t, J=7.6 Hz, 3H); 1.22 (t, J=7.6 Hz, 3H); 1.34-1.36 (m, 2H); 1.48-1.54 (m, 2H); 1.87-1.90 (m, 2H); 2.39 (t, J=7.6 Hz, 2H); 2.44-2.51 (m, 4H); 4.10 (q, J=7.6 Hz, 2H)

Example 81

Ethyl 2-(butylthio)acetate (33d)

Colorless oil (5.80 g, 100% yield). $^1$HNMR (400 MHz, CDCl$_3$): δ 0.89 (t, J=6.8 Hz, 3H); 1.26 (t, J=7.2 Hz, 3H); 1.36-1.41 (m, 2H); 1.52-1.61 (m, 2H); 2.61 (t, J=7.6 Hz, 2H); 3.18 (s, 2H); 4.15 (q, J=7.2 Hz, 2H)

General Procedure for Synthesis of Alkylthioether Carboxylic Acids (14) (Scheme 8)

To a stirred solution of alkylthioethercarboxylic acid ester (33) (0.1 mole, 1 eq) in ethanol (20 mL) was added 2N aq. NaOH (1.5 eq) dropwise into the reaction mixture. The reaction mixture was stirred room temperature for 30 min (the reaction progress is monitored by TLC). After the reaction was completed, the reaction mixture was concentrated on a rotavapor and the residue was cooled in ice bath. A few pieces of crushed ice were introduced into the flask and neutralized with 1N HCl. The product was extracted with ethyl acetate (20×20 mL). The combined extracts was dried over $Na_2SO_4$ and evaporated at 0° C. on rotavap. The residue was purified by silica gel column chromatography using hexane as eluents to get the pure alkylthioether carboxylic acids (14).

Example 82

4-(Ethylthio)butanoic Acid (14a)

Colorless oil (2.01 g, 90% yield). $^1$HNMR (400 MHz, $CDCl_3$): δ 1.26 (t, J=7.6 Hz, 3H); 1.84-1.92 (m, 2H); 2.40 (t, J=9.6 Hz, 2H); 2.47-2.55 (m, 4H); 10.92 (sbroad, 1H).

Example 83

2-(Butylthio)acetic Acid (14b)

Colorless oil (0.77g, 77% yield). $^1$HNMR (400 MHz, $CDCl_3$): δ 0.89 (t, J=7.6 Hz, 3H); 1.37-1.43 (m, 2H); 1.54-1.60 (m, 2H); 2.65 (t, J=7.6 Hz, 2H); 3.23 (s, 2H); 10.00 (sbroad, 1H).

Example 84

2-(Ethylthio)acetic Acid (14c)

Colorless oil (4.76g, 85% yield). $^1$HNMR (400 MHz, $CDCl_3$): δ 1.26 (t, J=7.6 Hz, 3H); 2.65 (q, J=7.6 Hz, 2H); 3.22 (s, 2H); 10.92 (sbroad, 1H).

Example 85

4-(Butylthio)butanoic Acid (14d)

Colorless oil (3.64g, 80% yield). $^1$HNMR (400 MHz, $CDCl_3$): δ 0.89 (t, J=7.6 Hz, 3H); 1.35-1.41 (m, 2H); 1.50-1.56 (m, 2H); 1.88-1.93 (m, 2H); 2.47-2.50 (m, 4H); 2.55 (t, J=7.2 Hz, 2H); 10.89 (sbroad, 1H).

Example 86

In Vitro Pharmacology Results:

The monoamine transporters inhibitory activities of selected cycloalkylmethylamines of Formula (I) are reported herein. The compounds were evaluated using well established radioligand binding assays protocols (Galli, A. et al., J. Exp. Biol. 1995, 198, 2197-2212; Giros, B. et al., Trends Pharmcol. Sci. 1993, 14, 43-49; Gu, H. et al., J. Biol. Chem. 1994, 269(10), 7124-7130; Shearman, L. P. et al, Am. J. Physiol., 1998, 275(6 Pt 1), C1621-1629; Wolf, W. A. et al., J. Biol. Chem. 1992, 267(29), 20820-20825). The human recombinant transporter proteins dopamine (DAT), norepinephrine (NET) and serotonin (SERT) were selected for the in vitro assays. The radioligand binding assays were carried out at 11 different test concentrations 0.1 nM to 1 μM.

The assays were carried out in duplicates and the quantitative data are reported as Ki in the Table 1.

| Example | Compound | DAT Ki (nM) | NET Ki (nM) | SERT Ki (nM) |
|---|---|---|---|---|
| 20 | 7g | 92.02 | 37.21 | 2.99 |
| 29 | 8a | 2.38 | 46.72 | 1.40 |
| 32 | 8d | 5.45 | 72.05 | 3.80 |
| 36 | 8h | 2.39 | 12.69 | 1.19 |
| 38 | 8j | 1.16 | 11.01 | 0.80 |
| 49 | 12b | 67.56 | 51.87 | 18.77 |
| 50 | 12c | 115.70 | 1422 | 3.31 |
| 54 | 13c | 23.93 | 17.07 | 14.84 |
| 55 | 13d | 104.20 | 51.03 | 65.33 |
| 57 | 13f | 49.19 | 119 | 224 |
| 61 | 17a | 29.45 | 44.72 | 38.40 |

What is claimed is:

1. A compound of structural Formula (I):

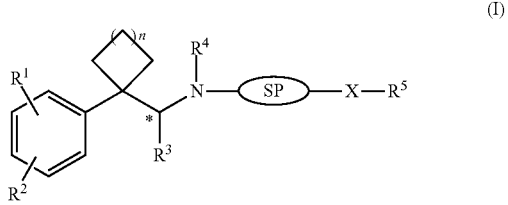

(I)

or a pharmaceutically acceptable salt thereof, wherein:
n is 1;
SP is a spacer of $C_4$ alkylene;
X is O or S;
$R^1$ and $R^2$ are independently H, $C_{1-6}$ alkoxy, or halogen;
$R^3$ is H or $C_{1-6}$ alkyl;
$R^4$ is H;
$R^5$ is $C_{1-6}$ alkyl;
optionally $R^1$-$R^5$ are independently substituted with $^2$H (deuterium); and
"*" denotes a carbon capable of being optically active.

2. The compound according to claim 1, wherein $R^1$ and $R^2$ are independently $C_{1-6}$ alkoxy or halogen.

3. The compound according to claim 1, wherein $R^1$ is H and $R^2$ is halogen or alkoxy.

4. The compound according to claim 1, wherein $R^5$ is ethyl.

5. The compound according to claim 1, wherein X=O.

6. The compound according to claim 1, wherein X=S.

7. The compound according to claim 6, wherein the compound is 1-(1-(4-chlorophenyl)cyclobutyl)-N-(4-(ethylthio)butyl)-3-methylbutan-1-amine.

8. The compound according to claim 6, wherein the compound is 1-(1-(3,4-dichlorophenyl)cyclobutyl)-N-(4-(ethylthio)butyl)-3-methylbutan-1-amine.

9. The compound according to claim 1, which is at least about in 95% enantiomeric excess in R-form over S-form.

10. The compound according to claim 9, which is an optical pure R-form.

11. The compound according to claim 1, which is at least about in 95% enantiomeric excess in S-form over R-form.

12. The compound according to claim 11, which is an optical pure S-form.

13. A pharmaceutical composition comprising the compound of claim 1 and a pharmaceutically acceptable vehicle.

* * * * *